(12) United States Patent
Grace et al.

(10) Patent No.: US 6,786,874 B2
(45) Date of Patent: *Sep. 7, 2004

(54) APPARATUS AND METHOD FOR THE COLLECTION OF INTERSTITIAL FLUIDS

(75) Inventors: John P. Grace, Lake Villa, IL (US); Neil W. Loomis, Racine, WI (US); Thomas G. Schapira, Bristol, WI (US); Sie Ting Wong, Mundelein, IL (US); Kristin M. Noonan, Chicago, IL (US); Michael G. Lowery, Wildwood, IL (US); Pete M. Bojan, Grayslake, IL (US); Daniel P. Schmidt, Bannockburn, IL (US); Tung-Ming Huang, Buffalo Grove, IL (US); Robert G. Hiltibran, deceased, late of Libertyville, IL (US), by Jon G. Hiltibran, legal representative; Mark R. Pope, Grayslake, IL (US); John J. Kotlarik, Lake Geneva, WI (US); Brian Joseph Tarkowski, Lake Villa, IL (US); David Dean Cunningham, Lake Villa, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/243,584

(22) Filed: Sep. 13, 2002

(65) Prior Publication Data

US 2003/0114774 A1 Jun. 19, 2003

Related U.S. Application Data

(63) Continuation of application No. 09/529,148, filed on Jan. 26, 2001, now Pat. No. 6,468,229.

(51) Int. Cl.[7] ............ A61B 10/00; B65D 81/00
(52) U.S. Cl. ........................................ 600/573
(58) Field of Search ....................... 600/573, 583, 600/578, 574–577, 579–582; 604/317; 606/180, 181, 182

(56) References Cited

U.S. PATENT DOCUMENTS

| | | | |
|---|---|---|---|
| 3,623,475 A | | 11/1971 | Sanz et al. |
| 3,626,929 A | | 12/1971 | Sanz et al. |
| 3,741,197 A | | 6/1973 | Sanz et al. |
| 5,582,184 A | | 12/1996 | Erickson et al. |
| 5,746,217 A | | 5/1998 | Erickson et al. |
| 5,820,570 A | | 10/1998 | Erickson et al. |
| 5,879,367 A | | 3/1999 | Latterell et al. |
| 5,885,211 A | | 3/1999 | Eppstein et al. |
| 6,015,392 A | * | 1/2000 | Douglas et al. ............. 600/583 |
| 6,468,229 B1 | * | 10/2002 | Grace et al. ................ 600/573 |

FOREIGN PATENT DOCUMENTS

| | | |
|---|---|---|
| WO | 9510223 | 4/1995 |
| WO | 9707734 | 3/1997 |
| WO | 9708987 | 3/1997 |

\* cited by examiner

*Primary Examiner*—Mary Beth Jones
*Assistant Examiner*—Brian Szmal
(74) *Attorney, Agent, or Firm*—David L. Weinstein

(57) ABSTRACT

The present invention involves apparatus and methods for use in collecting bodily fluids, such as interstitial fluids, from the epidermal layer of an animal. A preferred apparatus includes a pressure head and, optionally, a holder therefor for supplying a positive pressure to the head. The methods include the application of a positive pressure to the area surrounding an epidermal site from which stratum corneum has been breached, such as by laser ablation, to cause bodily fluids, such as interstitial fluids, to exude from the site and collecting the fluids exuding therefrom.

13 Claims, 20 Drawing Sheets

HEAD A

HEAD A

HEAD B

HEAD C

HEAD D

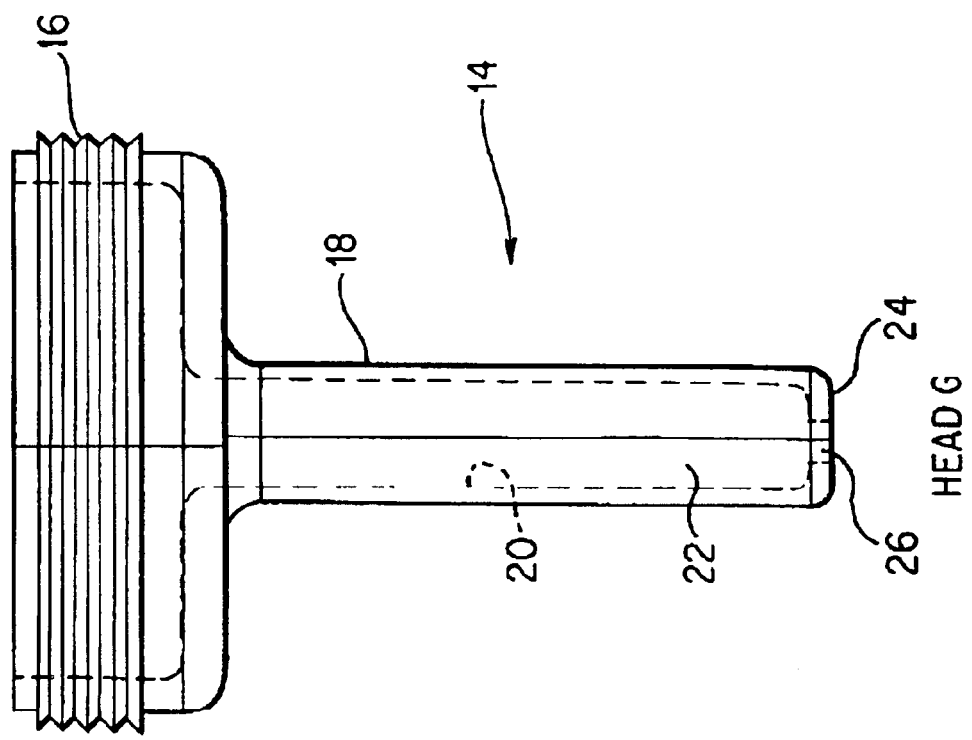

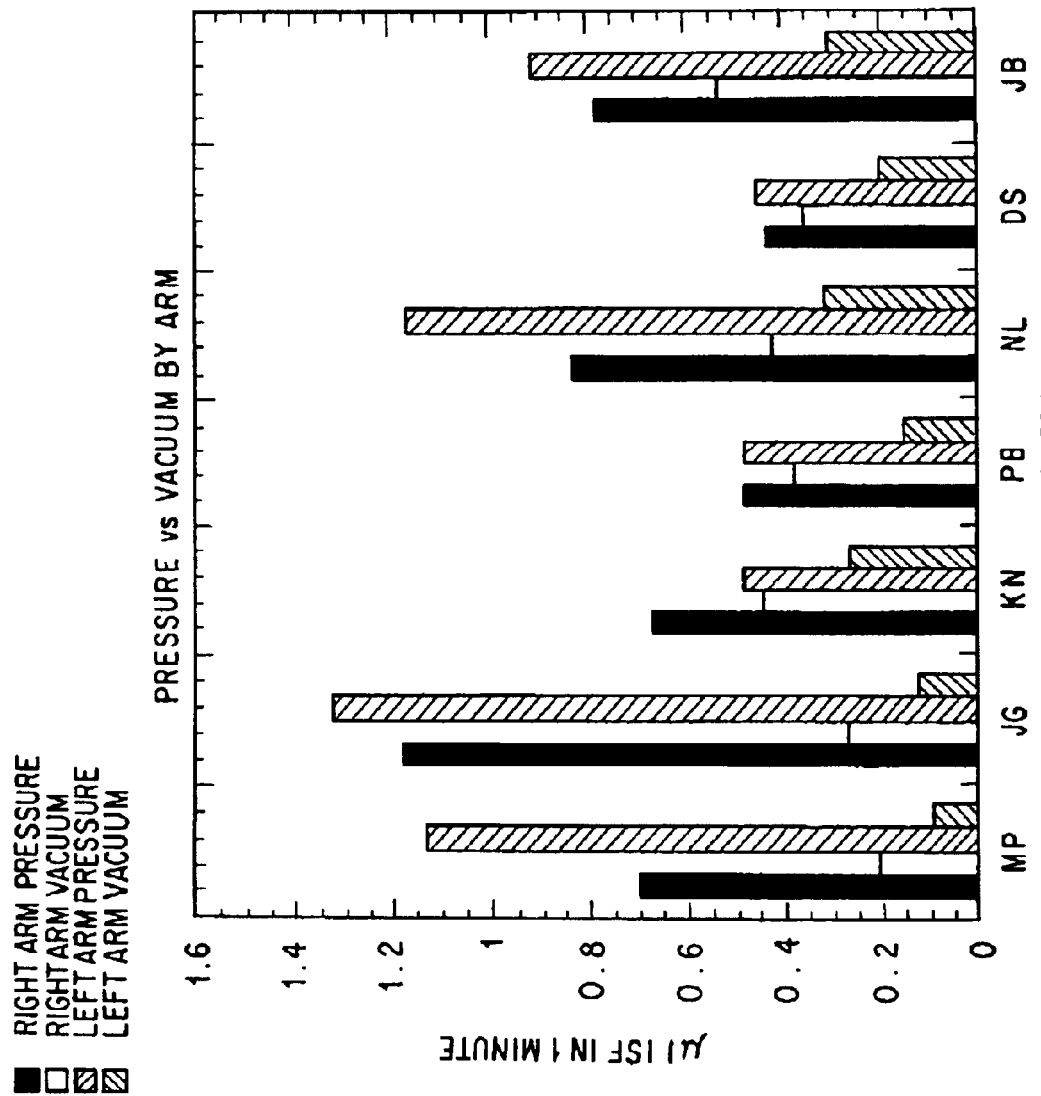

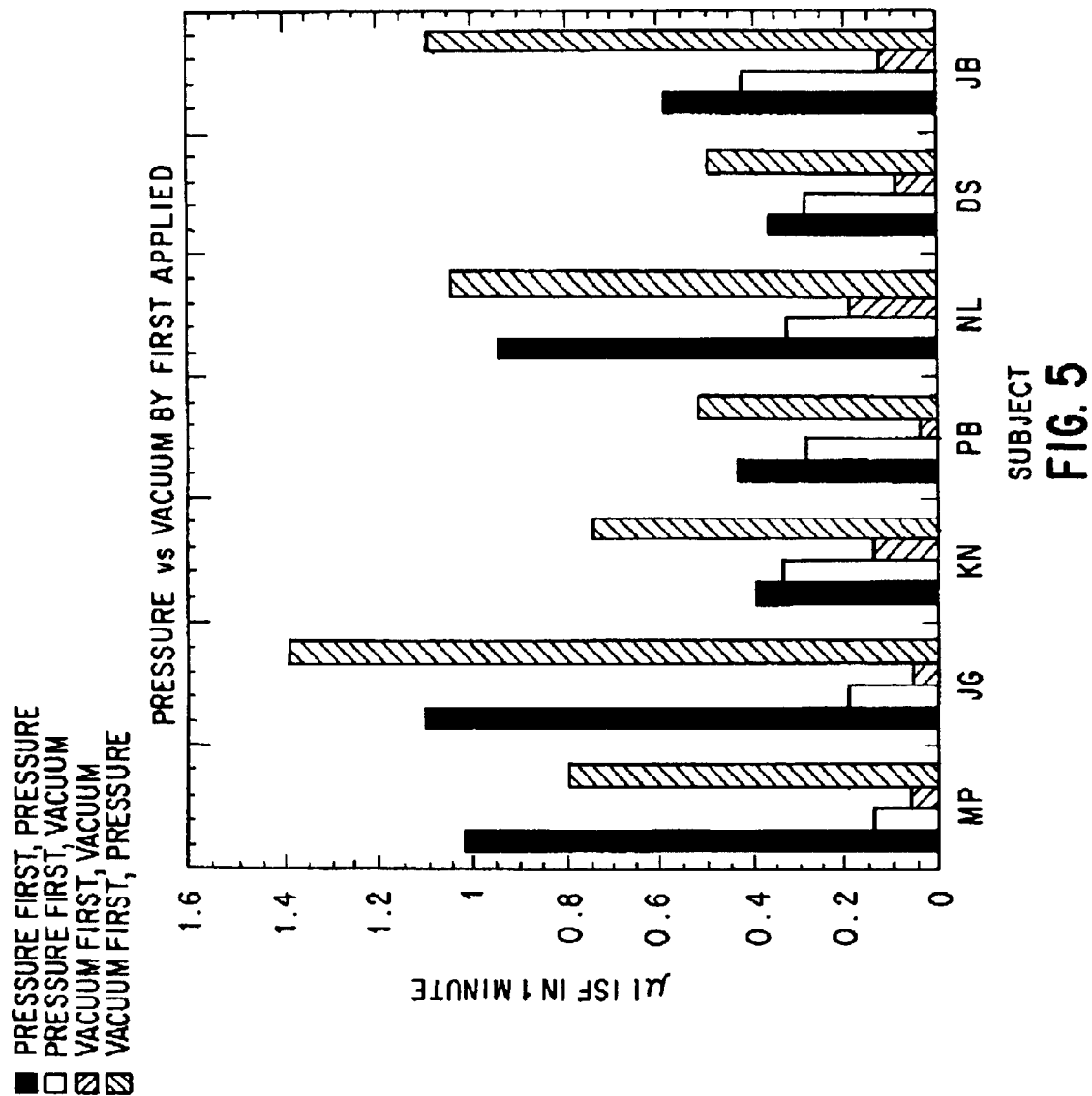

APPARATUS AND METHOD FOR THE COLLECTION OF INTERSTITIAL FLUIDS

This application is a continuation of U.S. application Ser. No. 09/529,148, having a filing date of Jan. 26, 2001 now U.S. Pat. No. 6,468,229.

BACKGROUND OF THE INVENTION

1. Field of the Invention

This invention relates to novel apparatus and methods for the collection of bodily fluids, such as interstitial fluids, from the body of an animal, such as a mammal. The fluids so collected may then be analyzed for biological or medical purposes, such as, for example, disease and health management activities. More particularly, this invention provides novel apparatus and methods for the collection of large quantities of interstitial fluids from areas of the skin where the stratum corneum has been breached.

2. Discussion of the Art

The stratum corneum is the outer horny layer of the skin comprising a complex structure of compact keratinized cell remnants separated by lipid domains. In humans, the stratum corneum typically has a thickness of about 10 $\mu$m to about 30 $\mu$m and overlays the epidermal layer, which itself has a thickness of on the order of about 100 $\mu$m. The dermal layer, found below the epidermal layer, contains, among other things, capillary networks through which blood flows.

It has been proposed that interstitial fluids can be obtained from the epidermal layer in a minimally invasive procedure by stripping away the stratum corneum to expose the epidermal layer and thereafter collecting interstitial fluids from the epidermis. Repeated application and removal of cellophane tape to the same location can be used to strip away the stratum corneum to expose the epidermal layer for the collection of interstitial fluids. Another technique available for the collection of interstitial fluids involves inserting a micro needle into the epidermal layer to allow fluids to be wicked up out of the body for deposit onto a membrane collection strip. This approach, however, requires precise insertion of the micro needle, oftentimes by trained medical personnel, and also results in biohazardous "sharps".

Another series of techniques for collecting interstitial fluids are described in PCT Patent Application, Ser. No. PCT/US96/13865, published on Mar. 6, 1997, International Publication No. WO97/07734 and the prior art cited therein (hereinafter referred to as the "PCT application"). The PCT application describes the use of energies at various wavelengths and frequencies to form micropores through the stratum corneum to a depth that exposes the epidermal layer. Methods to form such micropores include laser, sonic energy, and thermal energy, with or without the use of dyes or other energy absorbing materials to assist in the ablation and removal of the stratum corneum. In the PCT application, interstitial fluids are described as exuding from the epidermis after microporation of the stratum corneum. In addition, to induce fluid flow, a vacuum (10 to 12 inches of Hg) can be applied to the microporation sites (Examples 14 and 39 of the PCT application described above). Example 14 describes the use of the recovered fluids for analysis of biological materials, such as glucose levels. In Example 39, the use of a vacuum (i. e., a negative pressure) and ultrasound was said to produce an increase in the quantity of recovered interstitial fluid when compared with the use of vacuum alone.

In connection with the vacuum assist approach described in that PCT application, the volume collected is a function of the number of micropores, the level of vacuum, and the length of time the vacuum is applied. However, the techniques disclosed in the PCT application referred to above suffer from several disadvantages. First, even when all variables are optimized, the quantity of interstitial fluids obtained from the micropores in a short time period may not be sufficient to utilize in various medically related testing procedures. Second, increasing the applied vacuum above about 13 inches Hg (about −6.5 psig) can result in visible hematomas of the skin and patient discomfort. Moreover, the use of vacuum assistance increases the evaporation of the fluids under extraction and requires a substantially air-tight seal around the microporation site, which can oftentimes be difficult to achieve, even in a clinical setting. Finally, this technique also requires vacuum pumps and attendant fixtures, which can be expensive to acquire and maintain.

These and other disadvantages of the prior art are overcome by the apparatus and method of the present invention. In particular, the present invention provides apparatus and methods that allow the collection of large quantities of bodily fluids, such as interstitial fluids, from the epidermal layer over short periods of time, when compared with the amounts collectable through prior art techniques, without the need for vacuum assist devices. The apparatus and methods are inexpensive to fabricate, easy to use, and present minimal discomfort to the patient.

SUMMARY OF THE INVENTION

In the present invention, it has been discovered that increased amounts of interstitial fluids can be collected from micropores formed through the stratum corneum and extending into the epidermal layer by using a novel cup-shaped pressure head applied to the area of the skin surrounding the micropores. The pressure head is applied under a positive pressure, the force of which may fall within the broad range of about 1 to about 11 pounds, preferably from about 3 to about 11 pounds, with about 4 to about 9 pounds being preferred. The pressure head includes an aperture of diameter sufficient to surround the micropores, together with a reservoir volume in which the fluids may be collected and maintained and from which the fluids may be sampled or removed. The positive pressure may also be conveniently applied using the pressure head, with collection of fluids being carried out with separate apparatus, such as a capillary tube, an absorbent material, or other suitable device. The head may be housed in a holder having an air ram or other mechanism to provide variable pressure to the head when the head is placed on a patient's skin. The method of the present invention includes forming a breach through the stratum corneum and into the epidermal layer, followed by the application of a positive pressure to the area surrounding the microporation site to cause interstitial fluids to exude therefrom. The interstitial fluids are then collected.

BRIEF DESCRIPTION OF THE DRAWINGS

FIGS. 2A, 2B, 2C, 2D, 2E, 2F, and 2G are cross-sectional views of pressure heads of the present invention;

FIG. 4 is a graph of the data derived from Example 2;

FIG. 5 is a graph of the data derived from Example 2;

DETAILED DESCRIPTION

The present invention makes use of a pressure head that is positioned on the skin of an animal, such as a mammal, in a manner to encompass a site that has first been treated to breach the stratum corneum. Advantageously, the pressure head can be used in instances in which the stratum corneum has been removed by microporation techniques to expose the epidermal layer. Such microporation techniques are described in detail in the PCT application referred to above, which is incorporated herein by reference.

Figure 1:
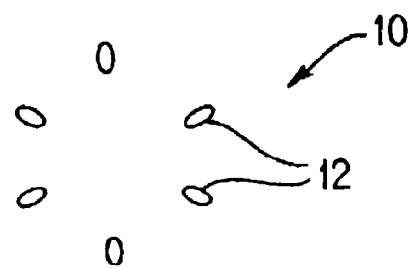
FIG. 1 is a typical microporation site having six micropores.

For example, the microporation technique may involve the use of focused laser energy of a power and pulse width sufficient to ablate the stratum corneum to expose the epidermal layer without substantial exposure of the dermal layer. This technique may be used with dyes or other energy absorbing materials to assist in the transfer of energy to the stratum corneum, and hence ablation of the stratum corneum, or may be used without such absorbing materials and may be applied to form one or more micropores, either sequentially or concurrently. Such micropores may be of circular, elliptical, or other shape. As used herein, the term "micropore" means a small breach or pore formed in the stratum corneum in a selected area of the skin to lessen the barrier properties of the stratum corneum such that fluids, for example interstitial fluids, can exude from the epidermal layer. Such micropores include those described in the PCT application referred to above and also include openings or breaches through the stratum corneum having diameters of on the order of up to 500 $\mu$m, with about 100 $\mu$m being preferred. For example, FIG. 1 shows a typical microporation site 10 that includes six micropores 12, each having an elliptical shape of about 80 $\mu$m by 100 $\mu$m in size. The overall size of the microporation site is about 1.5 mm when measured from the outer edges of the micropores 12. The centers of micropores 12 of FIG. 1 lie on a circle having a diameter of about 1 mm, with the centers of adjacent micropores being about 450 $\mu$m apart.

Prior art techniques for collecting interstitial fluids from a microporation site, such as site 10 of FIG. 1, involve either collecting the fluids as they naturally exude from the site or by providing a vacuum (i. e., negative pressure) to the site to cause more fluids to exude from the micropores 12. While these techniques permit the collection of some quantities of interstitial fluids, it has been discovered that significantly larger quantities of fluids can be collected in a shorter amount of time using the apparatus and methods of the present invention.

In particular, it has been discovered that the topical application of a positive pressure to the area surrounding the microporation site 10 permits recovery of interstitial fluids in an amount that is from about three (3) to about thirty (30) times or more than the amounts collected using the vacuum assist technique described above and in the PCT application referred to herein.

It has also been discovered that the positive pressure can advantageously be applied by using a generally cup-shaped pressure head that may be included in a holder that permits the application of variable amounts of positive pressure to the microporation site.

Thus, the present invention described herein can be utilized for the collection of interstitial fluids from a microporation site, irrespective of the techniques used to form the breach. Although the examples which follow below describe the use of the present apparatus and methods to collect fluids from micropores formed via laser energy, the invention is not so limited.

Referring now to FIGS. 2A through 2G, wherein like reference numerals refer to like components, various pressure heads of the present invention are generally depicted. The heads may be made from any suitable polymeric material, such as, for example acrylic, polypropylene, polyethylene, and others, including copolymeric and terpolymeric materials, as well as suitable metallic materials such as stainless steel, or such other materials suitable for formation of the head and application of pressure to the skin.

Figure 2A:
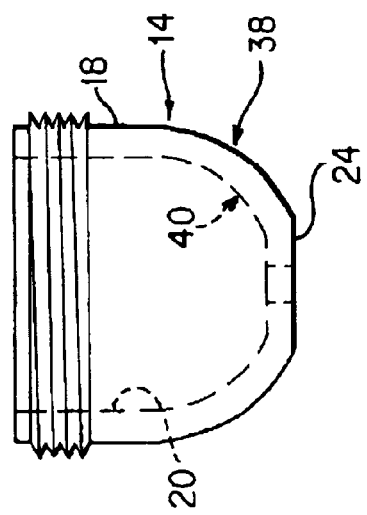
Figure 2B:
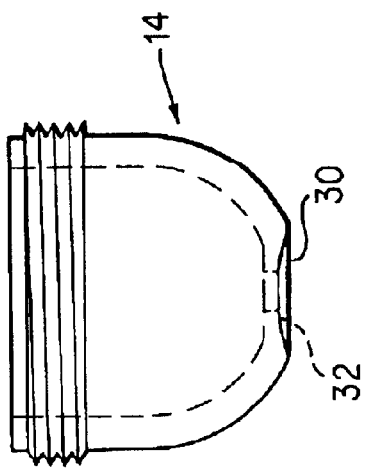
Figure 2C:
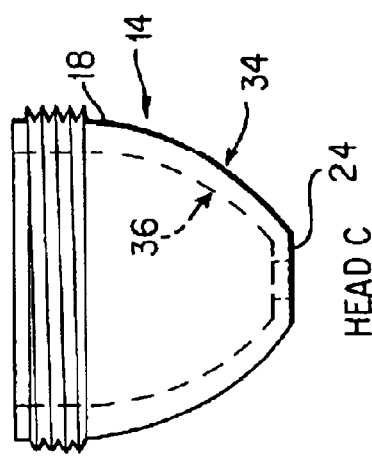
Figure 2D:
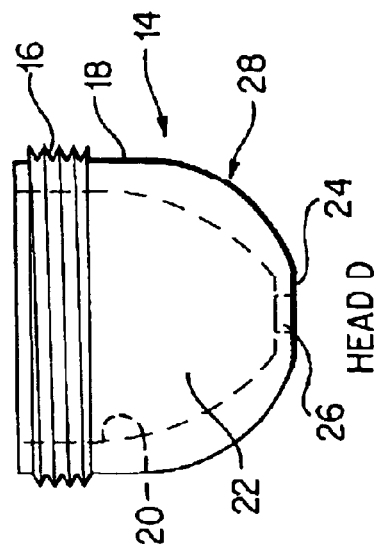

FIG. 2D depicts a pressure head 14 having at one end thereof a threaded end 16; preferably the threads are on the exterior wall 18 of the head 14, although the threads may also be along the interior wall 20. The interior of the head 14 forms a reservoir 22. The head 14, at the end opposite threaded end 16, includes a bottom portion 24 which may be circular, elliptical, square, rectangular or other shape. An aperture 26 is formed through the portion 24 to form a communication channel to the reservoir 22. In the head 14 of FIG. 2D, which is referred to in the examples that follow as "Head D", the radius of curvature 28 of the exterior wall 18 near the bottom portion 24 is 0.45 inches (11.43 mm), the bottom portion 24 being circular and having a diameter of 0.25 inches (6.35 mm), and the aperture being circular and having a diameter of 0.10 inches (2.54 mm). As explained hereinafter, it has been discovered that the radius of curvature of the exterior wall 18 near the bottom portion 24 has an effect on the quantities of interstitial fluids that can be collected from a microporation site.

FIG. 2B depicts a pressure head 14, referred to below as "Head B", which is similar to that shown in FIG. 2D; however, the bottom portion 30 of the pressure head of FIG. 2B is concave and has a radius of curvature 32 of 0.50 inches (12.7 mm), with the concave portion having a diameter of 0.311 inches (7.9 mm).

FIG. 2C depicts a pressure head 14, referred to below as "Head C". The exterior wall 18 of Head C has a radius of curvature 34 of 0.75 inches (19.05 mm) and the interior wall 30 of Head C has a corresponding radius of curvature 36 of 0.650 inches (16.51 mm). The bottom portion 24 of the head 14 of FIG. 2C is circular and has a diameter of 0.25 inches (6.35 mm).

FIG. 2A depicts pressure head 14, referred to below as "Head A". The exterior wall 18 of Head A has a radius of curvature 38 of 0.45 inches (11.43 mm) and the interior wall 20 of Head A has a radius of curvature 40 of 0.361 inches (9.17 mm). The bottom portion 24 of the head 14 of FIG. 2A has a diameter of 0.377 inches (9.58 mm).

Figure 2F:
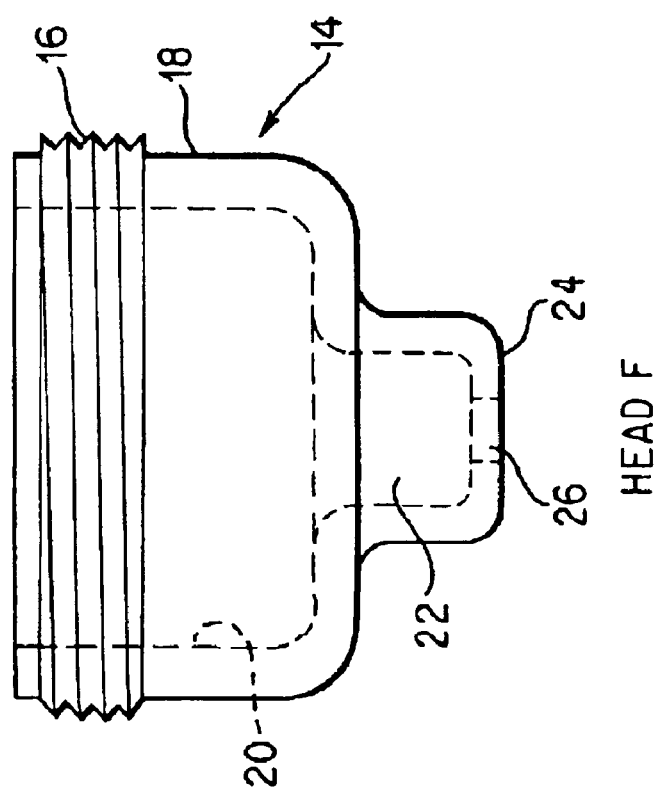
Figure 2E:
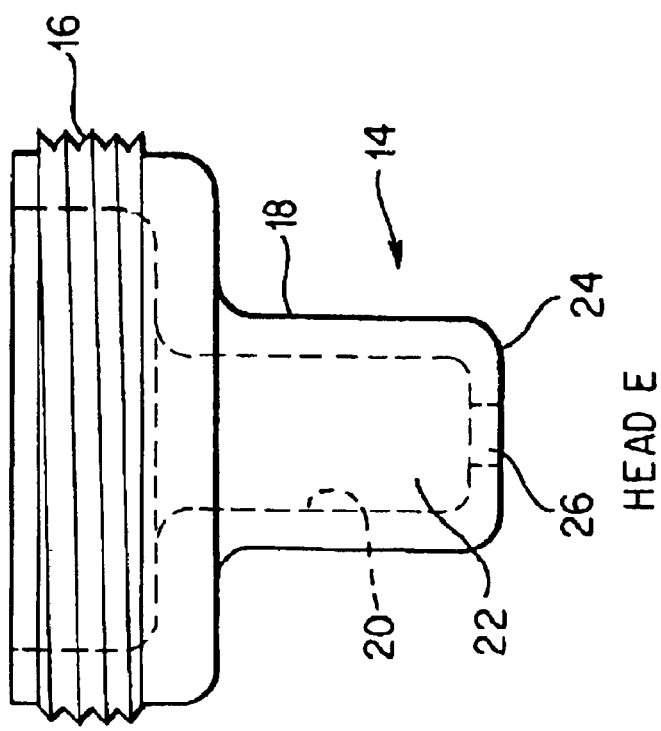

FIG. 2E depicts pressure head 14, referred to below as "Head E". The bottom portion 24 of the head 14 of FIG. 2A is circular and has a diameter of 9.5 mm.

FIG. 2F depicts pressure head 14, referred to below as "Head F". The bottom portion 24 of the head 14 of FIG. 2F has a diameter of 9.5 mm.

FIG. 2G depicts pressure-head 14, referred to below as "Head G". The bottom portion 24 of the head 14 of FIG. 2G has a diameter of 5.7 mm.

In the most general sense, the method of the present invention includes the steps of forming a breach through the stratum corneum and into the epidermal layer, followed by the application of a positive pressure to the area surrounding the microporation site to cause interstitial fluids to exude therefrom. The interstitial fluids are then collected. The fluids can then be analyzed to determine the concentration of an analyte, such as glucose. In operation, one specific method for the collection of interstitial fluids from the body of an animal comprises the steps of:

(a) forming a breach through the stratum corneum of the animal, such that the breach extends at least into the epidermal layer of the skin of the animal;

(b) placing a pressure head adjacent to the breach;

(c) exerting a positive pressure on the pressure head in a direction generally toward the skin of the animal; and (d) collecting fluids from the breach.

In this specific method, it is preferred that the pressure head be positioned such that the fluids flow through the aperture in the pressure head and into the reservoir.

Alternatively, another specific method for the collection of interstitial fluids from the body of an animal comprises the steps of:

(a) placing a pressure head against the skin of the animal;

(b) forming a breach through the stratum corneum of the animal such that the breach extends at least into the epidermal layer of the skin of the animal, the breach being adjacent to said pressure head;

(c) exerting a positive pressure on the pressure head in a direction generally toward the skin of the animal; and (d) collecting fluids from the breach.

A positive pressure can be exerted on the pressure head prior to forming the breach in the stratum corneum. In this specific method, it is preferred that the breach be formed so that it is in register with the aperture in the pressure head so that the fluids flow through the aperture in the pressure head and into the reservoir. Variations of these specific procedures can also be used.

In order to examine the efficiency of interstitial fluids collection using the pressure heads and methods of the present invention, a series of tests were performed, as described below.

EXAMPLE 1

In this example, nine (9) human volunteers were used. The interior forearms (between the elbow and the wrist) of each volunteer were subject to laser microporation (wavelength of 810 nm, 20 millisecond pulse width, approximately 250 milliwatts, 20 to 30 pulses applied, black tape applied to the skin to act as an energy absorber) to form a microporation site similar to microporation site 10 shown in FIG. 1. Two such sites were made on each arm of each subject and were hydrated with a water droplet placed on the microporation site for 10 to 15 seconds, followed by drying (using gentle blotting) prior to fluid extraction. Thus, a total of four microporation sites were made on each subject.

One site on the right arm and the corresponding site on the left arm of each subject were treated in the following manner. Head D, FIG. 2D, was manually placed over the microporation site so that the aperture 26 encompassed the site. Manual pressure was exerted on Head D in a direction toward the microporation site for sixty (60) seconds. Interstitial fluids flowed into Head D and were collected by means of 1 μl capillary tubes, with the collected volume recorded. By means of this technique, the volume of interstitial fluids recovered ranged from 0.34 to 1 μl.

The second site on the right arm and the corresponding second site on the left arm of each subject were treated as follows. A vacuum system, −7.5 psig (15 inches of Hg), was applied to each microporation site for 60 seconds. Interstitial fluids were observed to flow from the microporation site and were collected by means of 1 μl capillary tubes, with the collected volume recorded.

The interstitial fluids (hereinafter "ISF") collected by the application of positive pressure were thereafter analyzed for glucose levels. It is to be noted that for each use of the vacuum assist technique, the volume of interstitial fluids recovered was in the range of 0.1 to 0.2 μl and no glucose determination was made. As a control, a finger stick was also performed on each volunteer and approximately 50 μl of blood was withdrawn. The blood samples were centrifuged and the plasma analyzed for glucose values. Table 1 below presents the results of this example.

TABLE 1

| Volunteer ID* | ISF collected (μl) | Glucose in sample (mg/dl) |
|---|---|---|
| JK-1 | 0.73 | 153.29 |
| JK-2 | 0.74 | 135.27 |
| JK-3 | — | 124.4 |
| NL-1 | 0.77 | 147.01 |
| NL-2 | 1.36 | 150.00 |
| NL-3 | — | 129.6 |
| SW-1 | 0.36 | 260.56 |
| SW-2 | 0.34 | 275.88 |
| SW-3 | — | 270 |
| DS-1 | 0.34 | 126.76 |
| DS-2 | 0.50 | 136.60 |
| DS-3 | — | 115.9 |
| TM-1 | 0.63 | 124.60 |
| IM-2 | 0.87 | 124.94 |
| TM-3 | — | 126.1 |
| ML-1 | 1.00 | 96.00 |
| ML-2 | 0.45 | 111.33 |
| ML-3 | — | 103.5 |
| JG-1 | 0.89 | 126.97 |
| JG-2 | 1.35 | 111.04 |
| JG-3 | — | 104.1 |
| GH-1 | 0.92 | 90.43 |
| GH-2 | 0.53 | 93.21 |
| GH-3 | — | 91.1 |
| KN-1 | 0.69 | 103.91 |
| KN-2 | 0.68 | 113.24 |
| KN-3 | — | 94.8 |

*The number following each volunteer ID represents the following:
1 = left arm, pressure applied for 60 seconds;
2 = right arm, pressure applied for 60 seconds; and
3 = finger stick sample for comparison.

As can be seen from the foregoing table, the glucose values measured from the collected ISF are reasonably correlated to the glucose values obtained from the blood plasma. This example also demonstrates that the volume of ISF that can be obtained by the positive pressure technique disclosed herein is significantly greater than that obtained when using the vacuum method.

EXAMPLE 2

In this example, the sequential application of pressure followed by vacuum and vacuum followed by pressure was investigated. Two microporation sites, similar to FIG. 1, were made on each arm (left and right) of seven (7) human volunteers by means of the technique of Example 1. The microporation sites were hydrated as in Example 1 and were treated as follows. To one site on one arm (e. g., the right arm), Head D was applied, under manual pressure, for 60 seconds, ISF was collected, and the volume recorded. Thereafter, within two to five minutes, a vacuum system was used to apply a vacuum (13 inches Hg) to the same site for 60 seconds, ISF was collected, and the volume recorded. This pressure/vacuum technique was then applied to the corresponding site on the volunteer's left arm. To the second site on the first arm (e. g., the right arm) the vacuum system was first applied (13 inches Hg) for 60 seconds, ISF was collected, and the volume recorded. Thereafter, within two to five minutes, Head D was applied, under manual pressure, for 60 seconds to the same site, ISF was collected, and the volume recorded. This vacuum/pressure technique was then applied to the corresponding site on the volunteer's left arm in the same manner. Table 2 below presents the results of this example.

TABLE 2

| Volunteer ID | Arm | Condition* | Volume ISF (µl) collected under pressure | Volume ISF (µl) collected under vacuum |
|---|---|---|---|---|
| MP | Right | P/V | 0.79 | 0.18 |
|    | Left  | P/V | 1.25 | 0.11 |
|    | Right | V/P | 0.61 | 0.03 |
|    | Left  | V/P | 1.00 | 0.08 |
| JG | Right | P/V | 1.09 | 0.21 |
|    | Left  | P/V | 1.12 | 0.19 |
|    | Right | V/P | 1.26 | 0.07 |
|    | Left  | V/P | 1.52 | 0.05 |
| KN | Right | P/V | 0.45 | 0.34 |
|    | Left  | P/V | 0.35 | 0.34 |
|    | Right | V/P | 0.90 | 0.10 |
|    | Left  | V/P | 0.60 | 0.19 |
| PB | Right | P/V | 0.53 | 0.30 |
|    | Left  | P/V | 0.35 | 0.27 |
|    | Right | V/P | 0.44 | 0.06 |
|    | Left  | V/P | 0.61 | 0.02 |
| NL | Right | P/V | 0.75 | 0.30 |
|    | Left  | P/V | 1.15 | 0.36 |
|    | Right | V/P | 0.91 | 0.12 |
|    | Left  | V/P | 1.18 | 0.26 |
| DS | Right | P/V | 0.48 | 0.25 |
|    | Left  | P/V | 0.27 | 0.33 |
|    | Right | V/P | 0.38 | 0.10 |
|    | Left  | V/P | 0.63 | 0.07 |
| JB | Right | P/V | 0.71 | 0.38 |
|    | Left  | P/V | 0.48 | 0.48 |
|    | Right | V/P | 0.85 | 0.15 |
|    | Left  | V/P | 1.35 | 0.12 |

*P/V = Pressure followed by vacuum;
V/P = Vacuum followed by pressure

Figure 3:
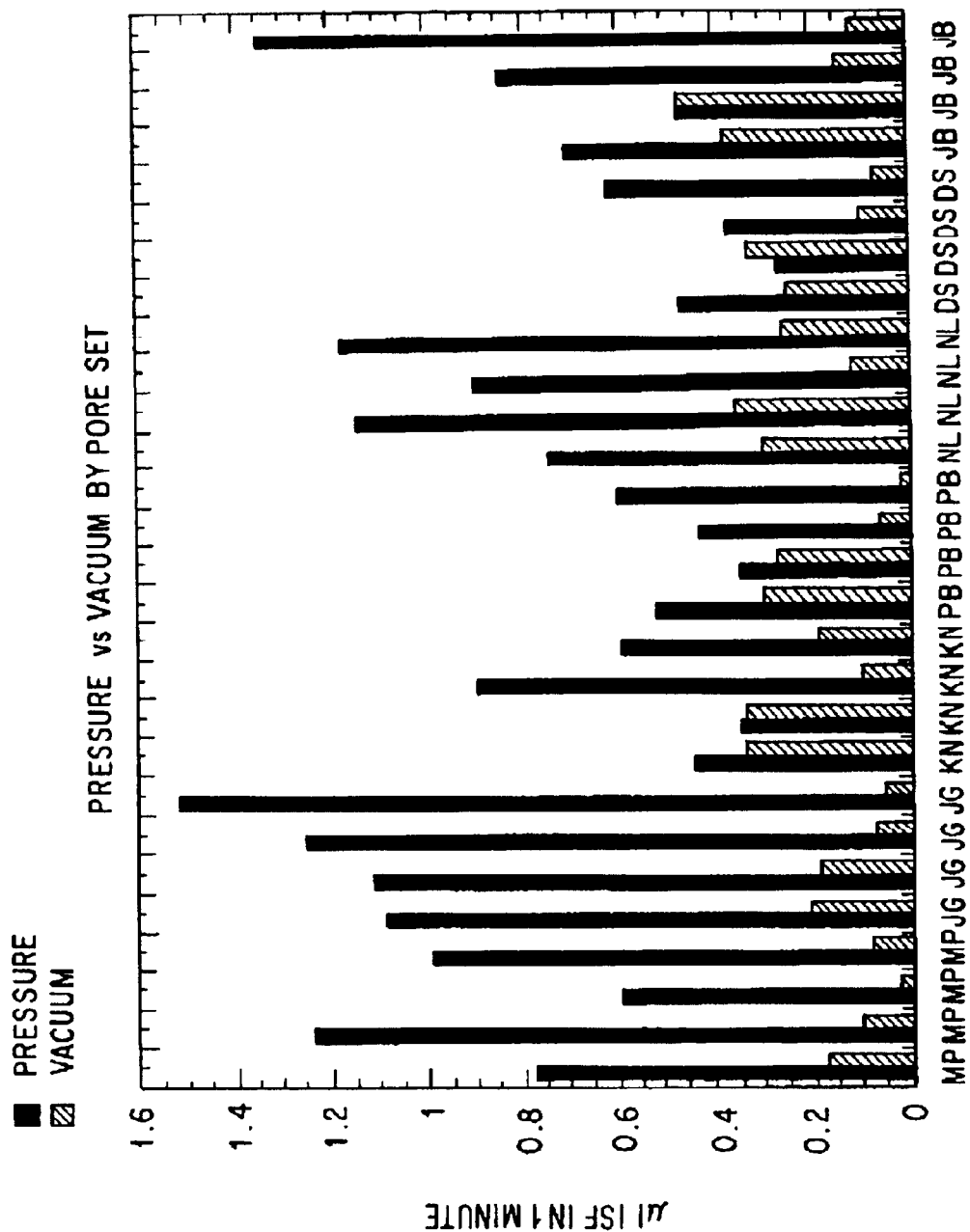
FIG. 3 is a graph of the data derived from Example 2.

As noted in Table 2, except for one instance involving volunteer DS, the application of pressure gave a greater volume of ISF than did vacuum, irrespective of whether the pressure was applied before or after the vacuum. These data are presented graphically in FIG. 3.

FIG. 4 presents these data in a slightly different form. As there shown, for example for volunteer MP, the average volume of ISF recovered from the right arm through the application of pressure is shown in the left most bar as 0.70 µl. This value is obtained from the foregoing table, where the ISF collected by the pressure technique is 0.79 µl and 0.61 µl from the right arm; the average is 0.70 µl. The remaining data found in FIG. 4 is determined in the same manner. FIG. 4 thus highlights that the use of positive pressure to obtain ISF is superior to vacuum techniques.

FIG. 5 is a further depiction of the data of Table 2 and again shows the distinct advantages of using positive pressure to obtain ISF. As there shown, the data are grouped by volunteer, according to the method first applied to collect ISF. For example, the left most bar in each data set represents the average volume of ISF collected from both arms of each volunteer during the 60 seconds of pressure application when pressure is applied first. For volunteer MP, this average value of 1.02 µl is obtained from the Table 2 data for the right and left arms (i. e., 0.79 µl and 1.25 µl respectively). The second bar represents the average value of ISF collected from both arms of volunteer MP during the 60 seconds of vacuum application when pressure is applied first. The third bar represents the average value of ISF collected from both arms of volunteer MP during the 60 seconds of vacuum application when vacuum is applied first, followed by pressure. Finally, the fourth bar represents the average value of ISF collected from both arms of volunteer MP during the 60 seconds of pressure application when vacuum is applied first. The data depicted in FIG. 5 for the remaining volunteers is obtained in a similar manner.

The means of the data set forth above in Table 2 also show that the application of positive pressure provides significant advantages to the collection of ISF over the vacuum technique. The following Table 3 sets forth the means of this data.

TABLE 3

| Volunteer ID | Mean ISF volume collected from both arms during 60 seconds of pressure application (µl) | Mean ISF volume collected from both arms during 60 seconds of vacuum application (µl) |
|---|---|---|
| MP | 0.91 | 0.10 |
| JG | 1.25 | 0.13 |
| KN | 0.57 | 0.24 |
| PB | 0.48 | 0.16 |
| NL | 1.00 | 0.26 |
| DS | 0.44 | 0.19 |
| JB | 0.85 | 0.28 |

Thus, for each volunteer, the use of positive pressure provided significantly higher ISF collection volumes than could be obtained from the use of vacuum. Indeed, across all volunteers, the mean collection volume of ISF was 0.78 µl by pressure but only 0.19 µl by vacuum, a difference of over 300%.

EXAMPLE 3

Figure 6:
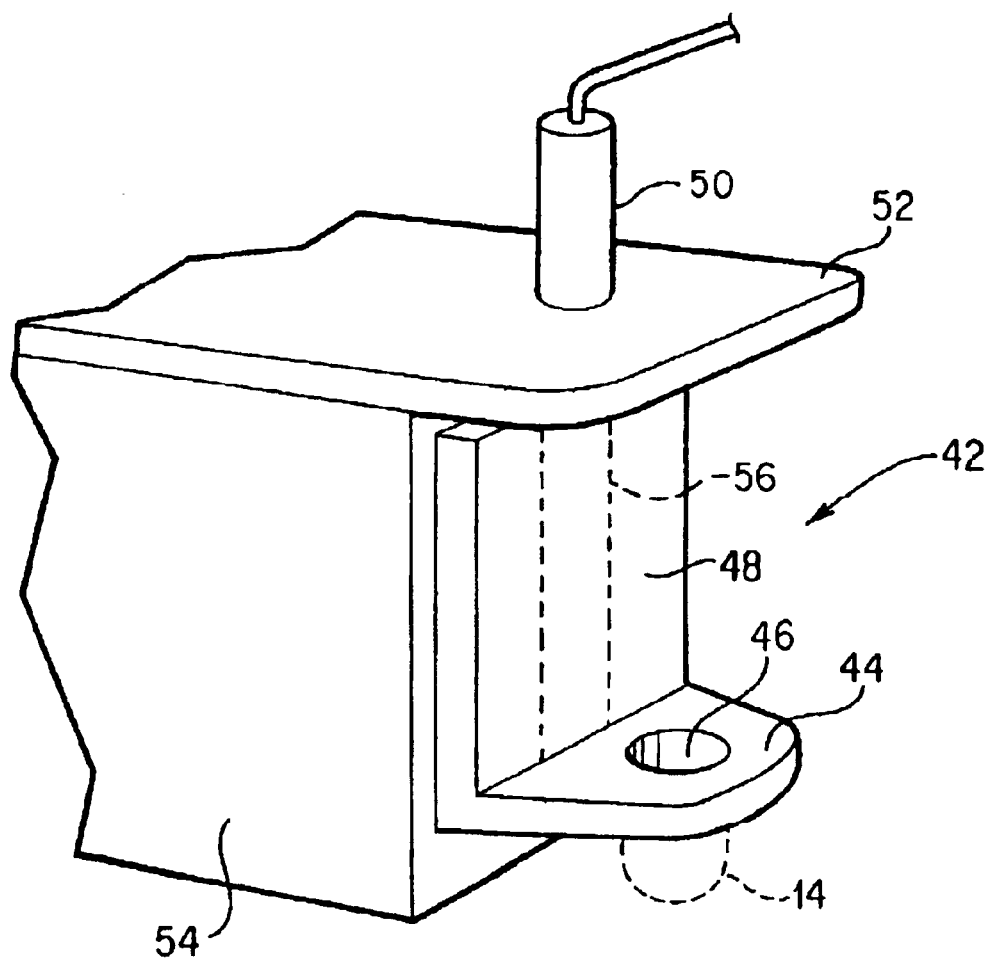
FIG. 6 depicts the holder and pressure head arrangement of the present invention.

As a follow-up to Examples 1 and 2, a further set of studies was performed on five (5) human volunteers. In these studies, microporation sites, similar to FIG. 1, were formed on the interior forearm of the volunteer by means of the technique of Example 1; the sites were hydrated as in Example 1. Head D (see FIG. 2D) was used as the pressure head and was attached to the holder 42 shown in FIG. 6. That holder includes a base plate 44 having a threaded opening 46 for engagement with the threaded end 16 of head 14 (shown in dotted lines in FIG. 6). The holder 42 also includes a movable vertical plate 48 attached to the base plate 44. The movable plate 48 is connected to a ram 50. The ram 50, which may be an air driven or hydraulic ram or a biased spring ram, operates to exert a force on the base plate 44, and hence to the threaded end 16 of the head 14. The ram 50, as depicted in FIG. 6, is coupled to a top plate 52, which in turn is coupled to a stand 54. Of course, other ways of connecting the ram 50 to the movable plate 48 can be used. The stand 54 may also be provided with a tongue (or groove) or other suitable mechanism for engagement with a groove (or tongue) or other suitable mechanism on the movable plate 48, as generally depicted by dotted lines 56 in FIG. 6. Such arrangement permits the movable plate 48 to travel in a repeatable manner when the holder 42 is used. The ram may exert a known force to the head 14, which force may be varied from one use of the holder to another or during any single use thereof. In this Example 3, the holder was operated such that a force of 4 through 11 pounds could be applied to the head 14 at the threaded end 16 thereof.

During the course of Example 3, the force applied to the threaded end 16 of Head D was maintained constant during any single run, but was varied from one run to the next. Thus, the following description of the tests performed on Subject 1 applies to the remaining subjects, unless otherwise noted.

After formation of the microporation site and hydration as in Example 1, Head D, having a circular bottom portion 24 with a diameter of 2.5 mm, was applied to the microporation site using a force of 5 pounds on the threaded end 16. The ISF flux (in μl/minute) was then measured in 30 second increments over an elapsed time of 6 minutes. Thereafter, Head D was removed from the microporation site. A new microporation site was formed and hydrated as in Example 1 and Head D was applied to this new site using a force of 6 pounds on the threaded end 16. The ISF flux (in μl/minute) was measured as described, after which Head D was again removed. Another microporation site was formed and the above procedure was repeated using a force of 7 pounds applied to the threaded end of Head D. The procedures were again repeated, as described, with the application of 8 and 9 pounds of pressure to the threaded end of Head D. Subjects 2 and 3 were treated as described above. Subject 4 was treated in the same manner, except that a force of 11 pounds on the threaded end 16 of Head D was also studied. Subject 5 was also treated in the same manner, except that the forces applied to the threaded end 16 of Head D were 4, 5, 6, 7 and 8 pounds.

This example also investigated the effect on ISF recovery caused by increasing the diameter of the bottom portion 24 of Head D. Thus, the procedures described above were used in conjunction with the Head D of FIG. 2D in which the diameter of the bottom portion 24 was 3.0 mm.

FIGS. 7A through 7J depict the results of this example, in which the flux rate of ISF is plotted against time (in minutes) for the applied forces and where the figures represent the diameters of the bottom portion 24 of Head D as described in the following Table 4.

TABLE 4

Figure 7A:
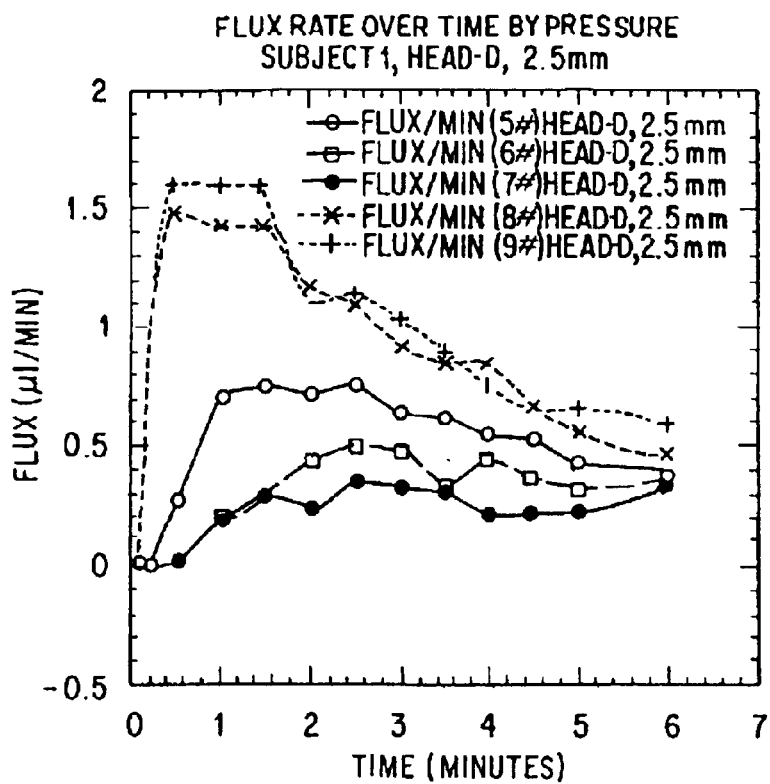
FIGS. 7A through 7J are graphs of the data derived from Example 3.
Figure 7B:
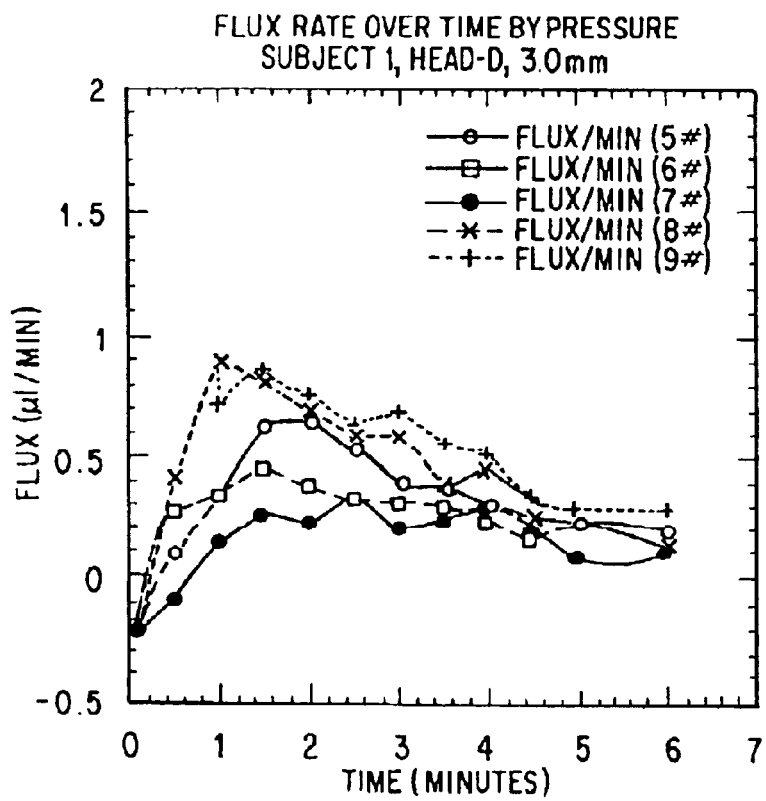
Figure 7C:
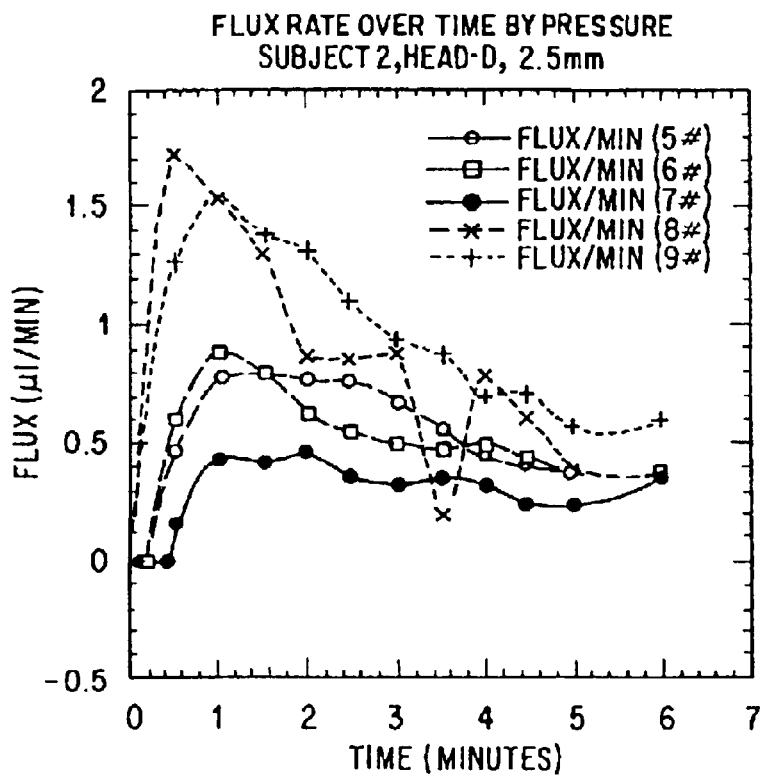
Figure 7D:
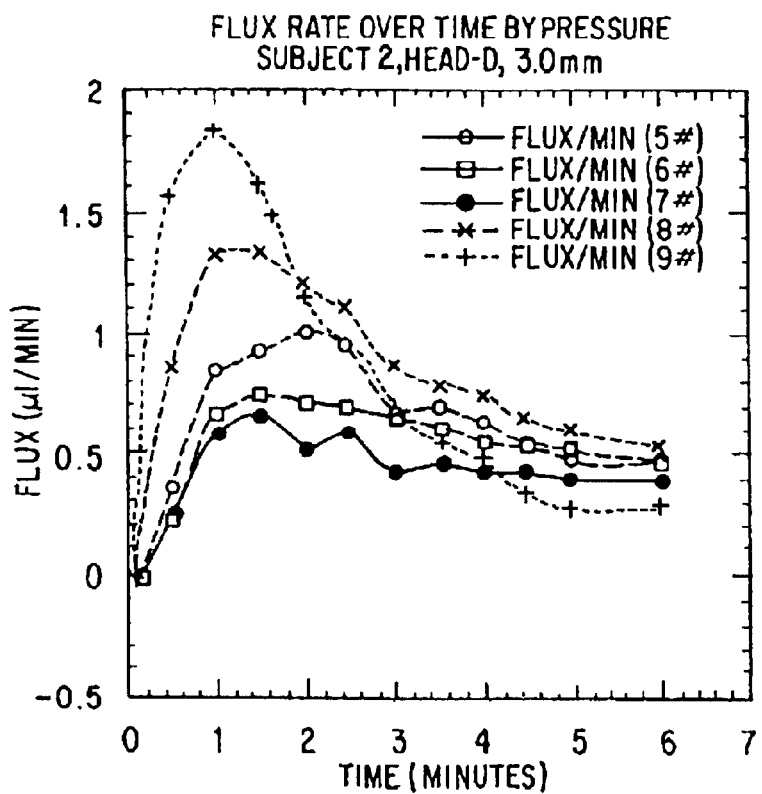
Figure 7E:
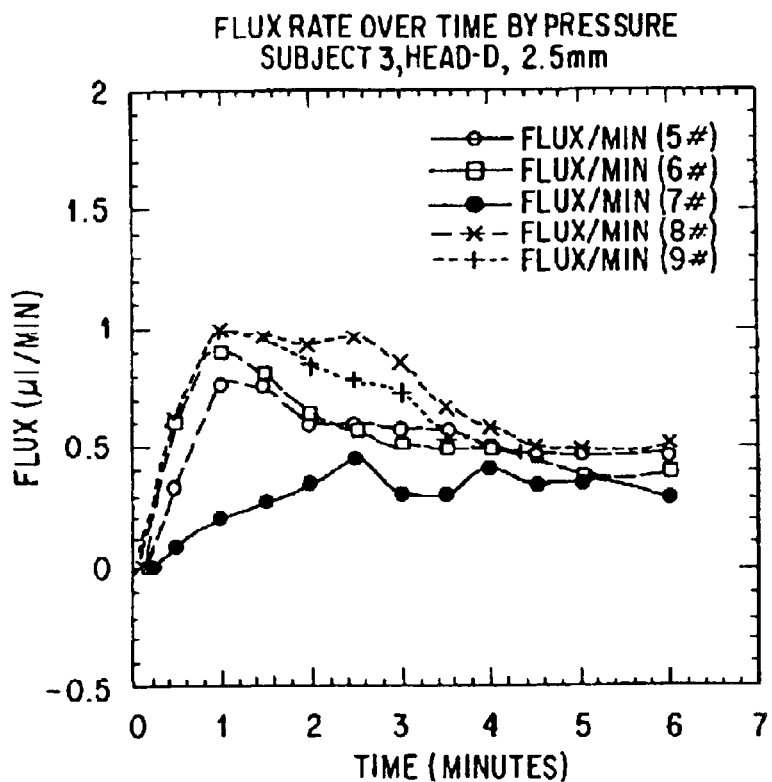
Figure 7F:
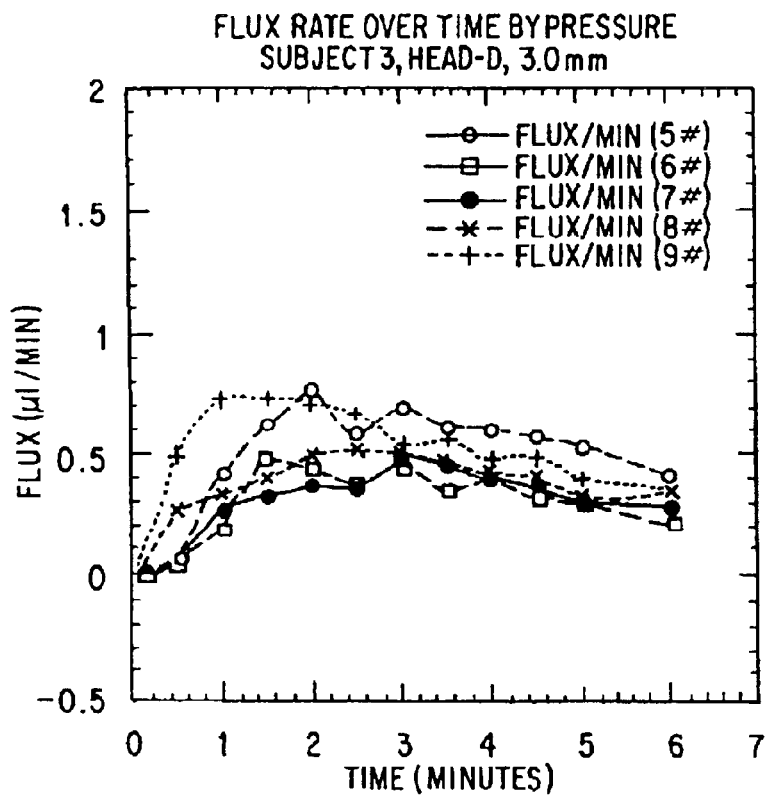
Figure 7G:
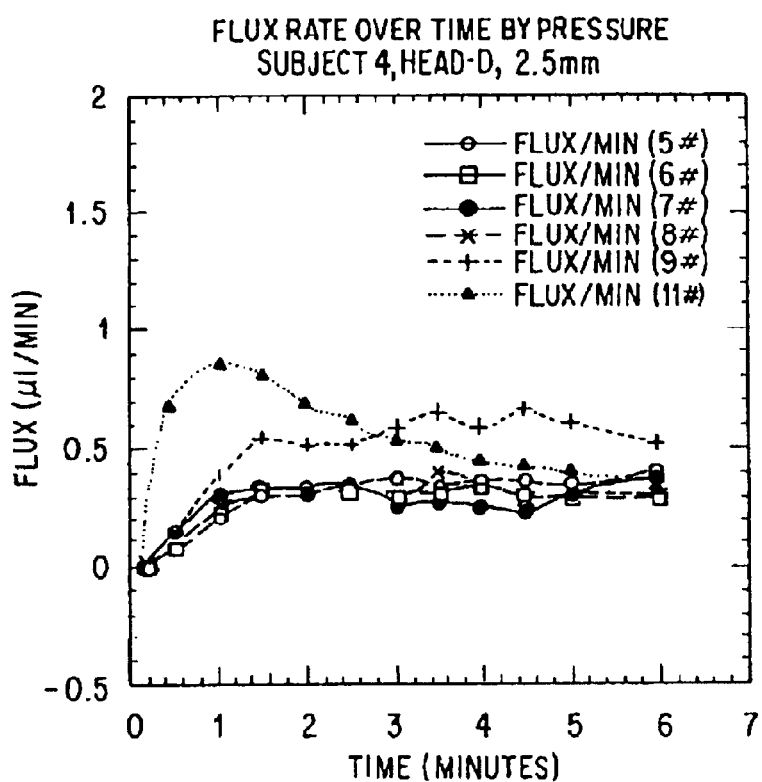
Figure 7H:
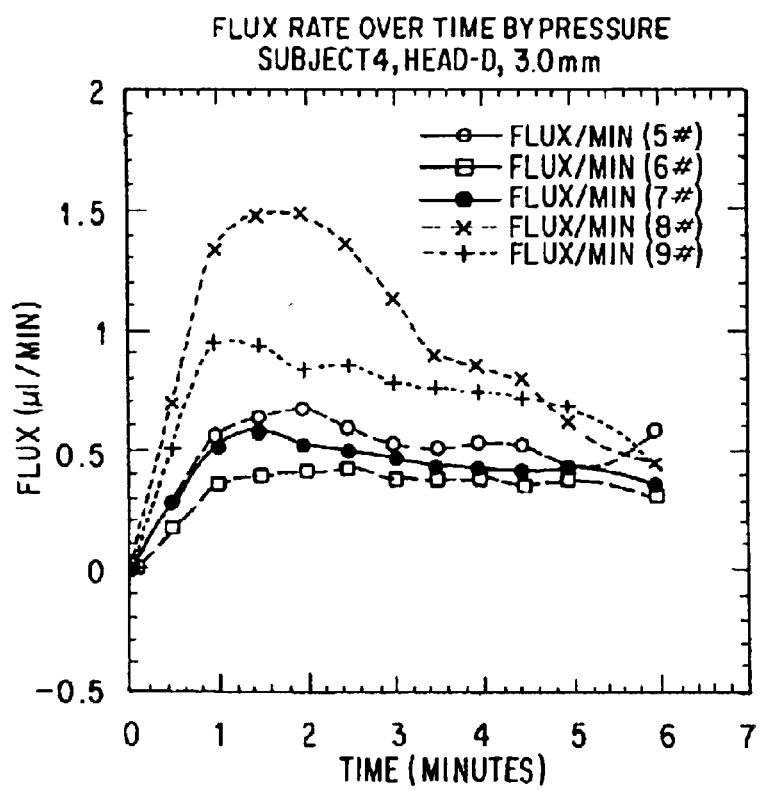
Figure 7I:
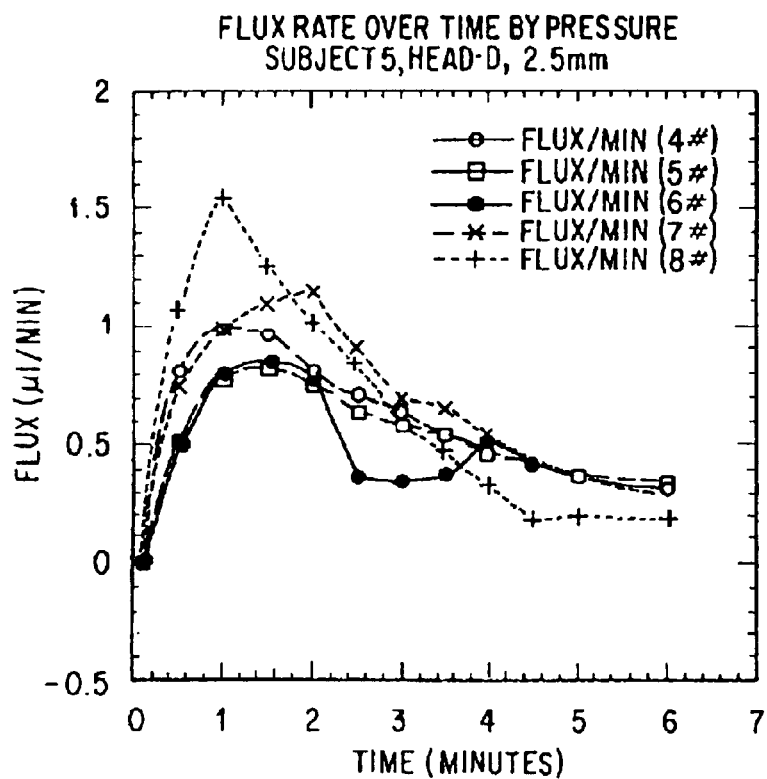
Figure 7J:
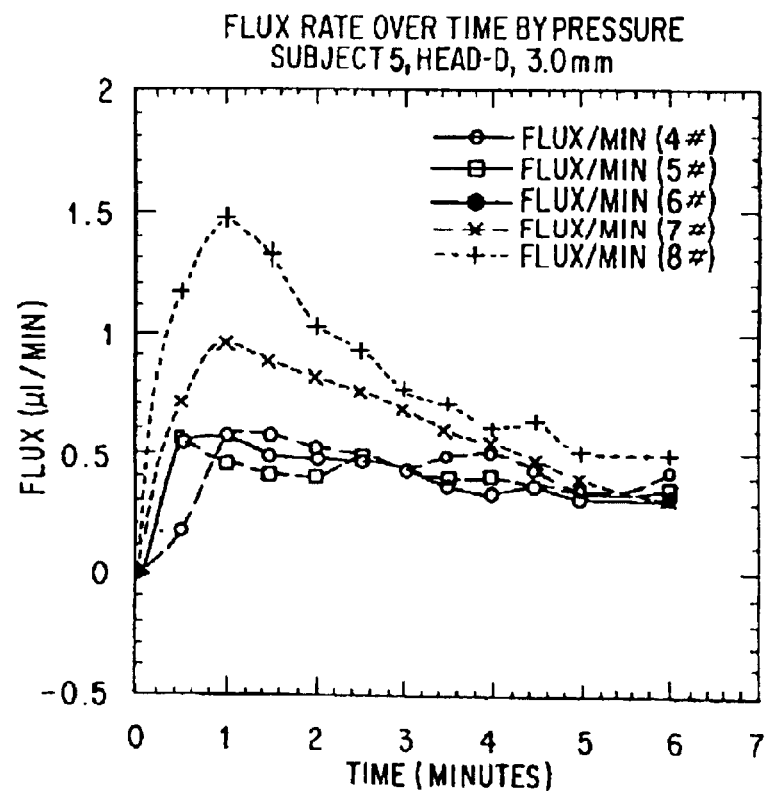

| Subject | 2.5 mm diameter | 3.0 mm diameter |
| --- | --- | --- |
| 1 | FIG. 7A | FIG. 7B |
| 2 | FIG. 7C | FIG. 7D |
| 3 | FIG. 7E | FIG. 7F |
| 4 | FIG. 7G | FIG. 7H* |
| 5 | FIG. 7I | FIG. 7J |

*Note:
11 pounds pressure not studied

Referring to FIGS. 7A, 7C, 7E, 7G, and 7I, it will be noted that, in most instances for each force applied, the rate of ISF flow increases for the first 60 seconds that the force is applied and then tends to decrease thereafter. However, there are some variations from subject to subject and, to a more limited extent, within the subjects themselves. The same general observations can be made from FIGS. 7B, 7D, 7F, 7H, and 7J.

Comparing the results obtained from using the 2.5 mm diameter Head D to those from using the 3.0 mm diameter Head D, it can be seen that for all subjects, except Subject 4, the initial rate of ISF flow was greater for the 2.5 mm diameter Head D.

EXAMPLE 4

In this example, Subjects 1, 3, and 6 of Example 3 were used to test the recovery rate of the ISF using a vacuum followed by the application of positive pressure. A microporation site was prepared and hydrated by means of the technique of Example 1 and the volume of recovered ISF was measured. For these subjects, ISF was collected for 120 seconds using vacuum (−12.73 psig), immediately followed by vacuum removal for 60 seconds for site recovery. After recovery, vacuum (−12.73 psig) was again applied for 120 seconds, followed by 60 seconds of site recovery (vacuum removed). This procedure was repeated five times using vacuum assistance. Each subject was then allowed a five minute recovery period, following which ISF was collected for 120 seconds using Head C with a force of 7 pounds applied to the threaded end 16 of Head C. Thereafter, Head C was removed from the microporation site for 60 seconds to allow for recovery. At the end of the collection period, ISF collection was performed for 120 seconds using Head C with a force of 7 pounds applied to the threaded end 16 of Head D. After this collection, Head C was removed for another recovery period of 60 seconds. Collection in this manner using positive pressure was carried out five times over the period.

Figure 8A:
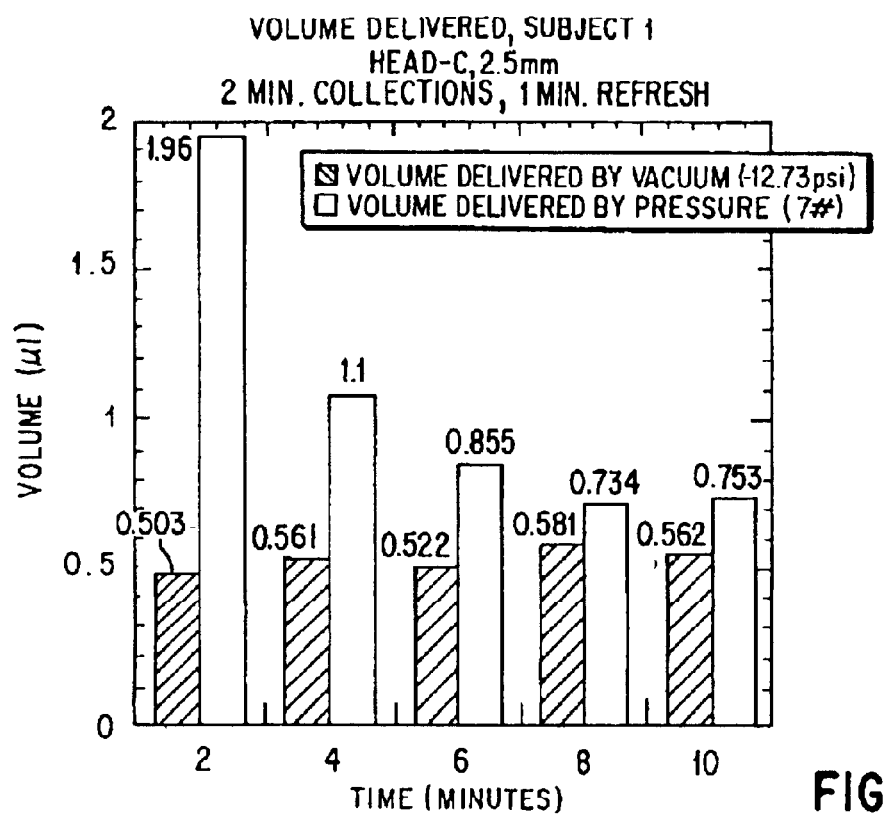
FIGS. 8A through 8C are graphs of the data derived from Example 4.
Figure 8B:
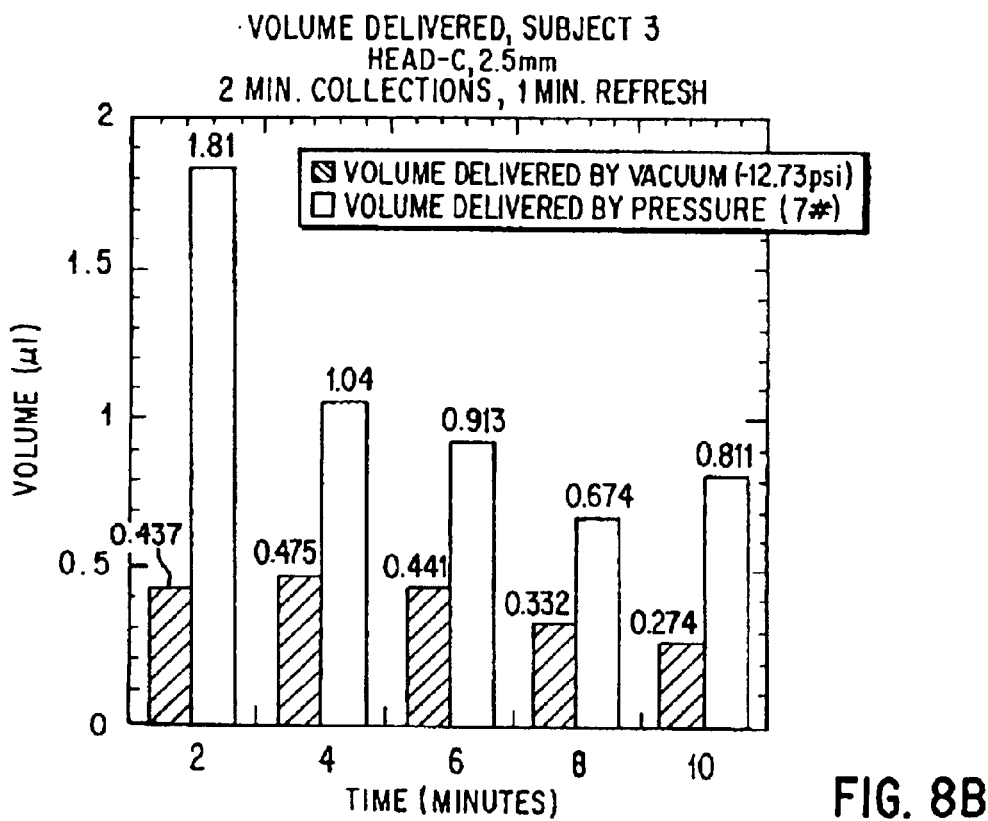
Figure 8C:
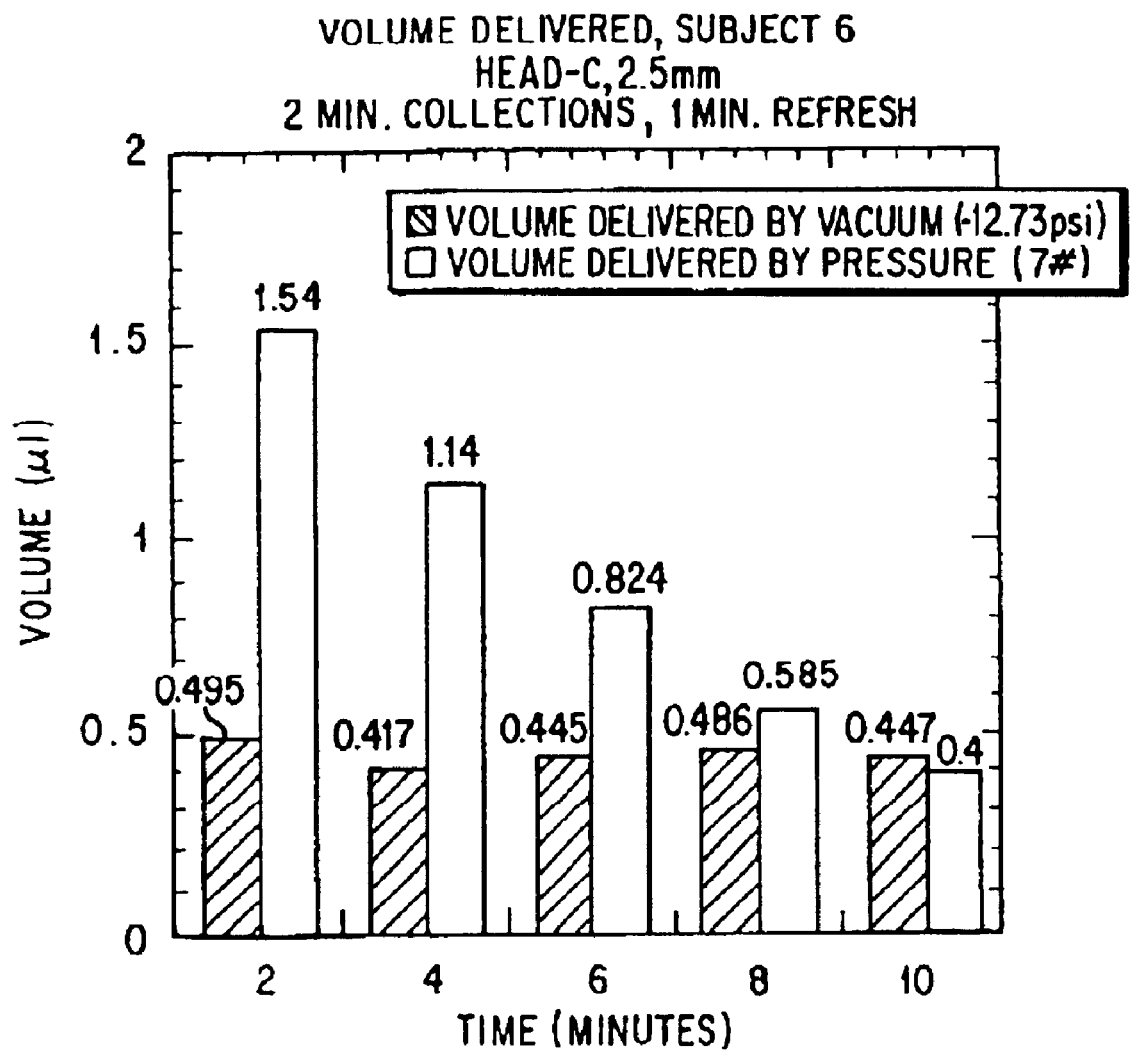
Figure 9A:
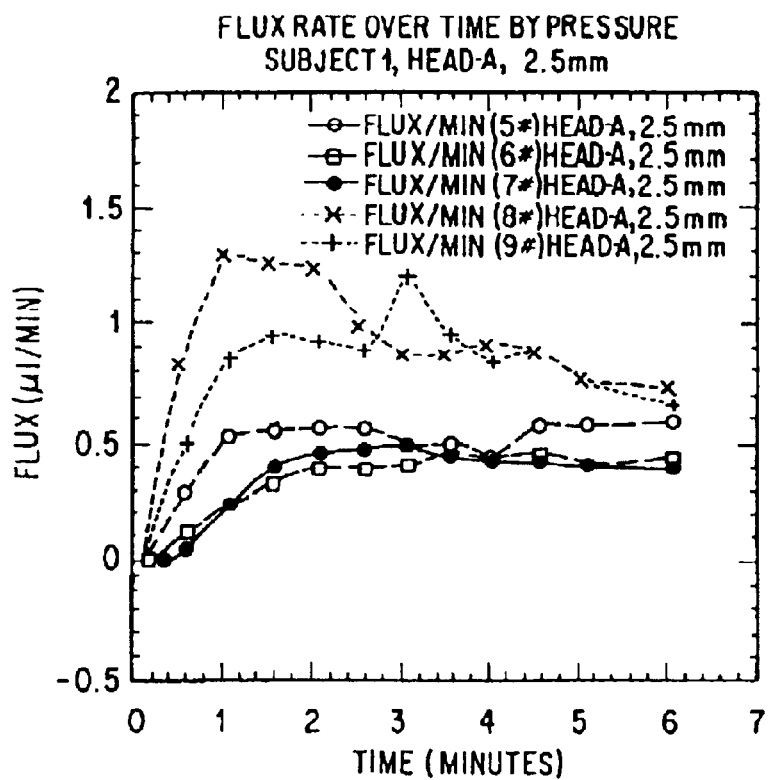
FIGS. 9A through 9H are graphs of the data derived from Example 5.
Figure 9B:
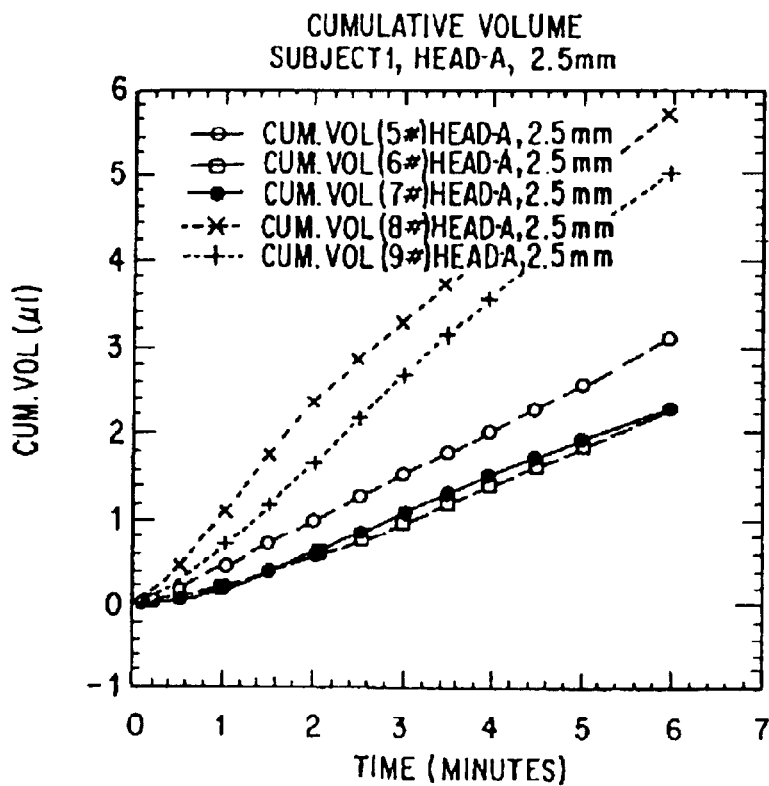
Figure 9C:
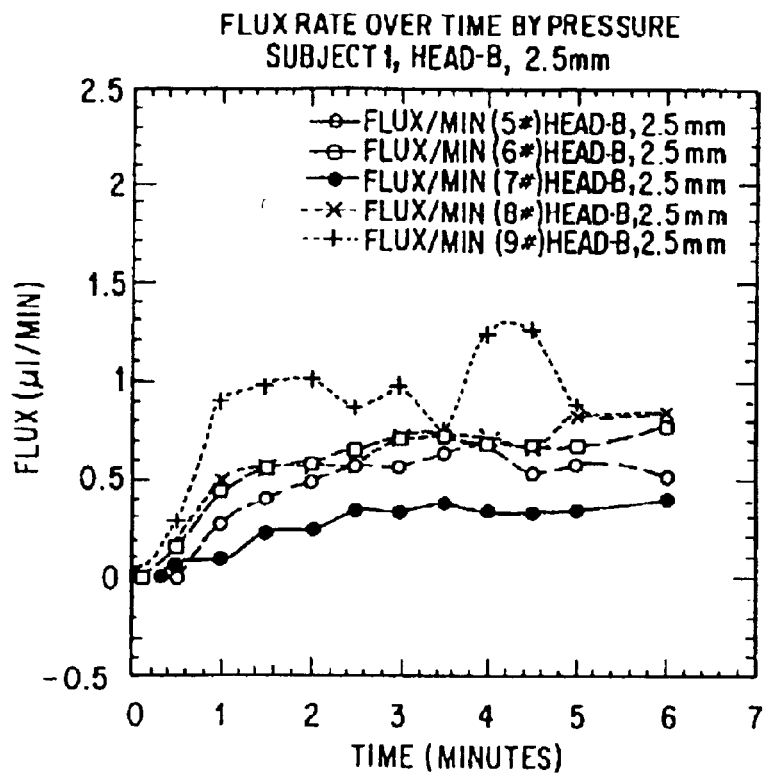
Figure 9D:
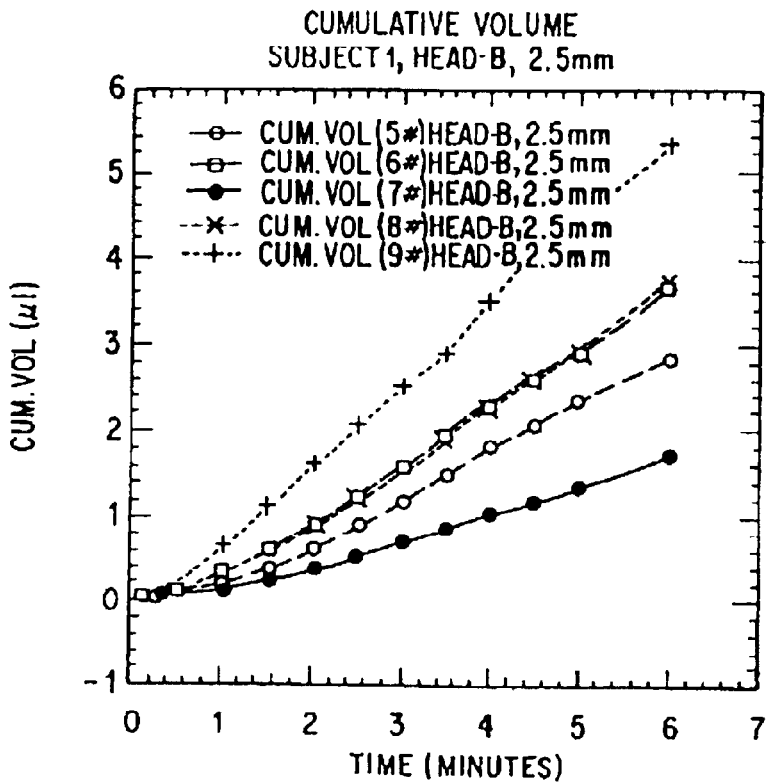
Figure 9E:
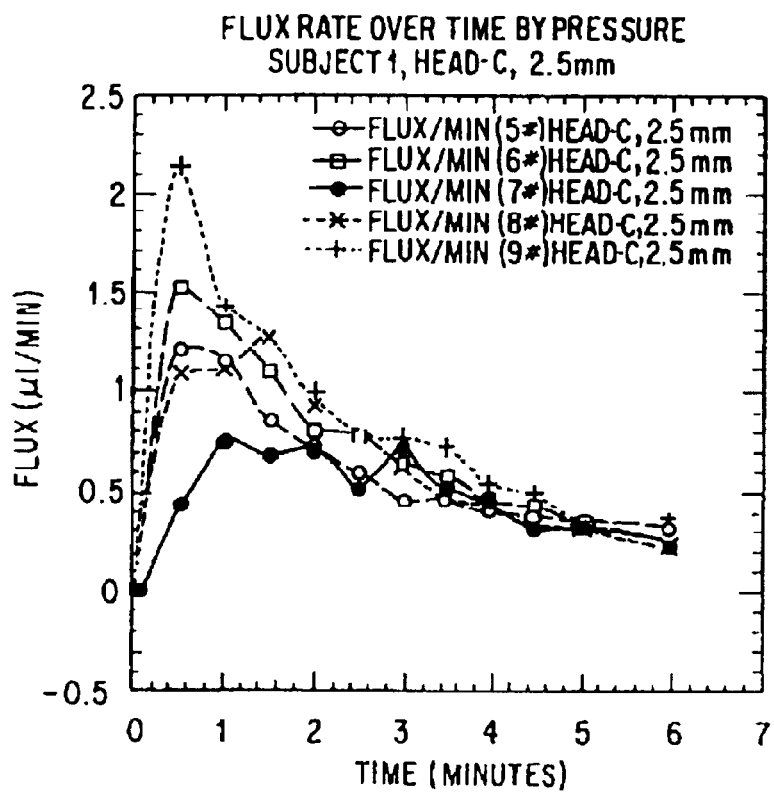
Figure 9F:
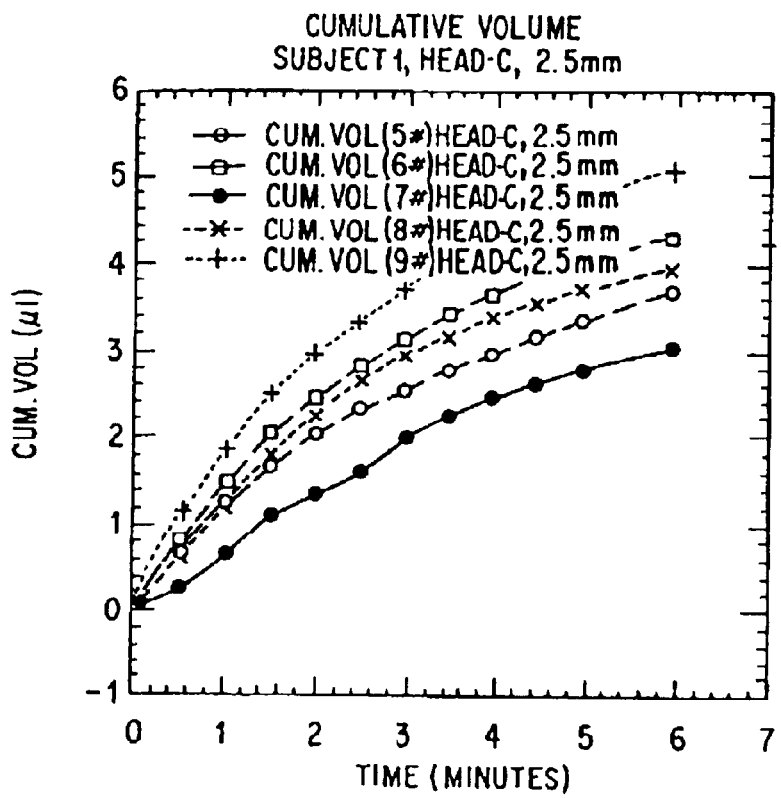
Figure 9G:
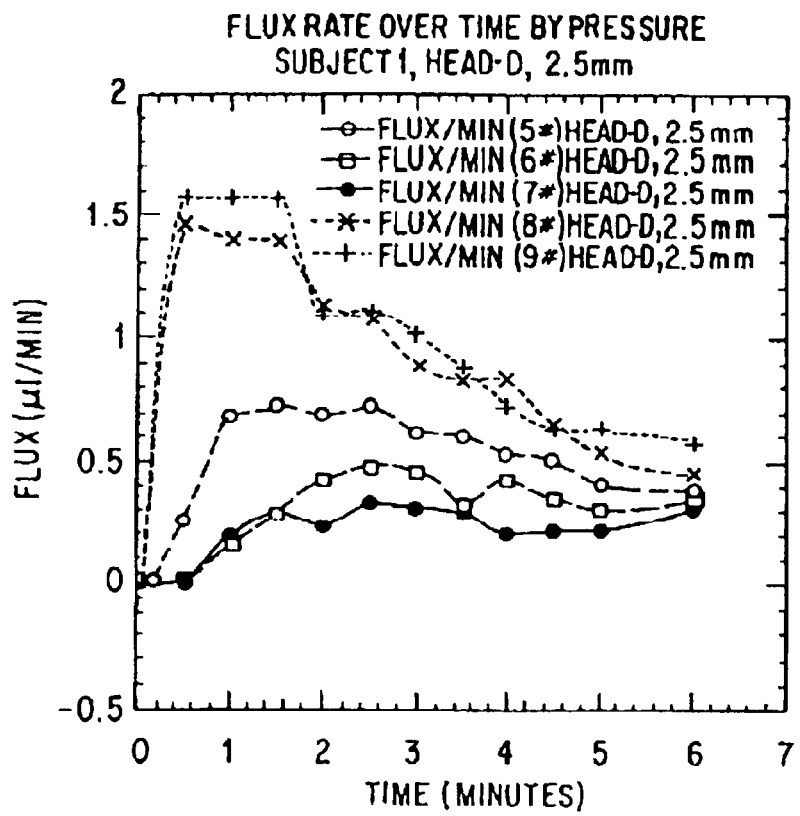
Figure 9H:
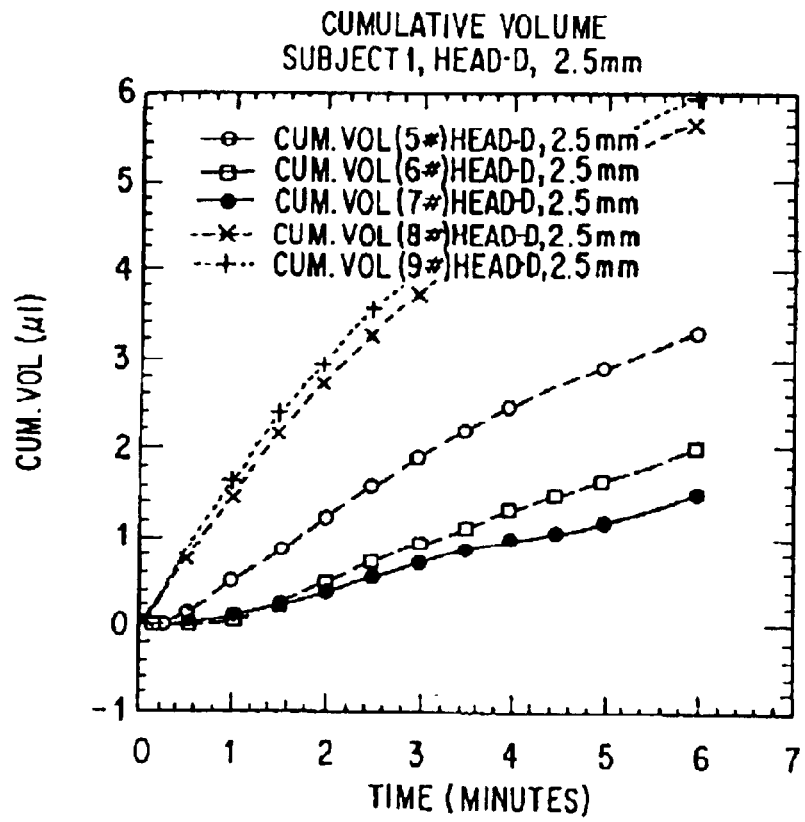

The results of this example are shown in FIGS. 8A through 8C. From FIGS. 8A through 8C, it is noted that the volume of ISF collected from each subject using the vacuum approach remained substantially constant over the test period, although the volume collected from Subject 3 decreased at 8 minutes and 10 minutes.

On the other hand, the volume collected from each subject upon the application of positive pressure generally decreased over the entire test period of 10 minutes. It is thus theorized that the ISF in the epidermis exists in equilibrium with fluids in the underlying dermal layer and the surrounding tissues. Removing large quantities of ISF from the epidermis and dermis over a relatively short period of time, without providing a sufficient recovery period, upsets this equilibrium and depletes the ISF residing in the epidermis and dermis of the treated area. Indeed, in connection with the present invention, it has been observed that when a recovery period of on the order of 3 to 8 minutes is used, the next removal of ISF by application of positive pressure will be of a high volume. For example, with reference to FIG. 8A, had the recovery time between the 6 minute and 8 minute positive pressure data been longer than the 60 seconds used, the volume of ISF recovered at 8 minutes would have been of the magnitude shown for the 2 minute pressure data. This result has led to the theory that there two mechanisms affecting the quantity of ISF in the epidermis. First, ISF naturally resides in the epidermal and dermal layers and is available to be removed upon the application of pressure. Second, there is a steady influx of ISF consisting of blood plasma filtrate from the capillaries, through the dermal layer, and into the epidermis. Although this influx occurs at a finite rate, this observation establishes the ability to continuously monitor ISF for fluid analysis and other purposes.

EXAMPLE 5

In this example, Heads A through D (see FIGS. 2A–2D), each having an aperture diameter of 2.5 mm, were used to collect ISF from Subject 1 of Example 3. A microporation site was prepared by means of the technique of Example 1 and ISF was collected by means of the technique described in Example 3. The rate of ISF removal and the volume of ISF removed was measured. FIGS. 9A through 9H set forth the flux rate and cumulative recovered volume data obtained in this example. As seen from a comparison of FIGS. 9A, 9C, 9E, and 9G, the Head C generally provides the greatest initial flow (i. e., slope) of ISF over the first 60 seconds as compared to Heads A, B and D. As observed from FIGS. 9B, 9D, 9F, and 9H, the Head C also provides the greatest volume of ISF collected over all applied pressures as compared to the other heads.

These data thus indicate that the head shape, particularly the radius of curvature, has an effect on the flow rate and volume of ISF recovered. In particular, as the shape of the exterior wall 18 of the pressure head 14 approaches that of a cylinder (i. e., no curvature along the longitudinal axis of the head when viewed from the threaded end 16 to the bottom portion 24), the rate of ISF flow and the volume of ISF recovered increases.

EXAMPLE 6

In this example, six different head configurations were used to extract ISF. Twelve microporation sites, similar to those of FIG. 1, were made on the interior forearms of five human volunteers by means of the technique of Example 1. Heads were attached to the holder 42 shown in FIG. 6. Head A was attached to the holder and was used to apply four (4) pounds force to the microporation site in the same manner as in Example 3. Another microporation site was then formed and head A was used to apply six (6) pounds of force to the microporation site. This process was repeated in this fashion until all heads, A B, C, D, E, and F were used on each subject. In each case, the ram fixture was used as in Example 3. ISF flux (in µl/minute) was then measured in 30-second increments over a five-minute period.

Table 5 shows the results of this experiment, including the average amount of ISF collected for all five subjects, for the times of 30 seconds and 60 seconds. Table 5 also shows the percentage of the total amount of ISF collected in 60 seconds that was collected in the first 30 seconds. This percentage indicates how quickly the rate of collection increases to its maximum and is pertinent because it is desirable for the instrument to collect the fluid in a short amount of time.

In this example, the micropores were arranged (a) singly, (b) in a straight line separated by 1 mm, or (c) in a triangle with each micropore forming a vertex of an equilateral triangle 1 mm on each side. Heads C, E, and G were used. The force was either four (4) pounds or seven (7) pounds for each combination of pore number and head. A fixture similar to the ram fixture was used, but instead of compressed air, this fixture utilized a system of weights applied to the top of the ram to deliver the force. This change was made to increase the accuracy of the force delivery and to reduce friction in the force delivery device. Fluid was collected for one minute at intervals of 30 second (if possible) and the volume collected was calculated.

Table 6 below shows the results of this example, including the average amount of ISF collected for all five subjects, for the times of 30 seconds and 60 seconds. Table 6 also shows the percentage of the total amount of ISF collected in 60 seconds that was collected in the first 30 seconds. This percentage indicates how quickly the rate of collection increases to its maximum and is pertinent because it is

TABLE 5

| Head | Force (pounds) | Average volume collected (µl) | Std. Dev. (µl) | RSD* (%) | Median volume collected (µl) | Percent of fluid collected in first 30 seconds | Percent of collections >1 µl | Percent of collections >0.5 µl |
|---|---|---|---|---|---|---|---|---|
| A | 4 | 0.23 | 0.22 | 96 | 0.16 | 12 | 0 | 20 |
| A | 6 | 0.41 | 0.37 | 89 | 0.45 | 31 | 0 | 40 |
| B | 4 | 0.15 | 0.18 | 115 | 0.08 | 29 | 0 | 0 |
| B | 6 | 0.11 | 0.13 | 112 | 0.08 | 6 | 0 | 0 |
| C | 4 | 0.52 | 0.40 | 77 | 0.35 | 35 | 20 | 40 |
| C | 6 | 0.93 | 0.29 | 32 | 1.10 | 39 | 60 | 80 |
| D | 4 | 0.38 | 0.40 | 103 | 0.23 | 28 | 20 | 20 |
| D | 6 | 0.48 | 0.25 | 51 | 0.44 | 34 | 0 | 40 |
| E | 4 | 1.03 | 0.24 | 23 | 1.02 | 44 | 60 | 100 |
| E | 6 | 1.44 | 0.48 | 34 | 1.42 | 44 | 80 | 100 |
| F | 4 | 1.12 | 0.43 | 38 | 0.98 | 43 | 40 | 100 |
| F | 6 | 1.92 | 0.43 | 23 | 2.07 | 43 | 100 | 100 |

*RSD means standard deviation (Std. Dev.) divided by average volume collected times 100%.

Total amount of fluid collected (µl):
Subject 1:10.72
Subject 2:9.39
Subject 3: 8.45
Subject 4: 4.49
Subject 11: 10.66

EXAMPLE 7

In this example, 18 microporation sites, as in Example 1, were made on the interior forearms of six human volunteers.

desirable for the instrument to collect the fluid in a short amount of time. The final column shows the increase in volume of fluid collected in one minute in the presence of additional micropores relative to volume of fluid collected in the presence of a single micropore. In general terms, the percentage increase in going from one micropore to two micropores was greater than the percentage increase in going from two micropores to three micropores. This was especially true of the more aggressive heads (head E and head G).

TABLE 6

| Head | Force (pounds) | Number of pores | Average volume collected (µl) | Std. Dev. (µl) | RSD* (%) | Percent of fluid collected in first 30 seconds | Percent of collections >1 µl | Percent of collections >0.5 µl | Ratio of amount collected compared to amount collected with 1 pore |
|---|---|---|---|---|---|---|---|---|---|
| C | 4 | 1 | 0.47 | 0.24 | 51 | 45 | 0 | 50 | 1.00 |
| C | 4 | 2 | 0.80 | 0.31 | 39 | 38 | 20 | 80 | 1.70 |
| C | 4 | 3 | 1.00 | 0.43 | 44 | 42 | 60 | 80 | 2.10 |
| C | 7 | 1 | 0.88 | 0.42 | 48 | 47 | 20 | 80 | 1.00 |
| C | 7 | 2 | 1.06 | 0.23 | 21 | 47 | 50 | 100 | 1.20 |
| C | 7 | 3 | 1.57 | 0.47 | 30 | 52 | 80 | 100 | 1.80 |

TABLE 6-continued

| Head | Force (pounds) | Number of pores | Average volume collected (µl) | Std. Dev. (µl) | RSD* (%) | Percent of fluid collected in first 30 seconds | Percent of collections >1 µl | Percent of collections >0.5 µl | Ratio of amount collected compared to amount collected with 1 pore |
|---|---|---|---|---|---|---|---|---|---|
| E | 4 | 1 | 0.79 | 0.22 | 28 | 44 | 10 | 90 | 1.00 |
| E | 4 | 2 | 1.27 | 0.47 | 37 | 40 | 60 | 100 | 1.60 |
| E | 4 | 3 | 1.86 | 0.58 | 31 | 43 | 100 | 100 | 2.30 |
| E | 7 | 1 | 1.22 | 0.22 | 18 | 53 | 90 | 100 | 1.00 |
| E | 7 | 2 | 2.29 | 0.51 | 22 | 54 | 100 | 100 | 1.90 |
| E | 7 | 3 | 2.99 | 0.57 | 19 | 48 | 100 | 100 | 2.50 |
| G | 4 | 1 | 1.75 | 0.41 | 23 | | 100 | 100 | 1.00 |
| G | 4 | 2 | 2.50 | 0.38 | 15 | | 100 | 100 | 1.40 |
| G | 4 | 3 | 2.58 | 0.47 | 18 | | 100 | 100 | 1.50 |
| G | 7 | 1 | 2.59 | 0.34 | 13 | | 100 | 100 | 1.00 |
| G | 7 | 2 | 3.04 | 0.59 | 19 | | 100 | 100 | 1.20 |
| G | 7 | 3 | 3.51 | 0.62 | 18 | | 100 | 100 | 1.40 |

*RSD means standard deviation (Std. Dev.) divided by average volume collected times 100%.

Total amount of fluid collected (µl):
Subject 1: 40
Subject 2: 55
Subject 4: 46
Subject 8: 44
Subject 11: 45

EXAMPLE 8

This example shows the effect of aperture diameter on the amount of fluid collected and the rate at which [the greatest percentage of fluid] is recovered. In this example, 11 head configurations were tested on the interior forearm of five subjects. The configurations were as follows:

| Head | Diameter of aperture (mm) |
|---|---|
| C | 1.5 |
| C | 2.5 |
| C | 3.0 |
| C | 4.0 |
| E | 1.5 |
| E | 2.5 |
| E | 3.0 |
| E | 4.0 |
| G | 1.5 |
| G | 2.5 |
| G | 3.0 |

Three micropores were arranged in a triangle, with each micropore forming a vertex of an equilateral triangle 1 mm on each side. Four pounds of force was used for each extraction. Each extraction had a duration of 60 seconds, with samples being collected at 30 and 60 seconds.

Table 7 shows the results of this experiment, including the average amount of ISF collected for all five subjects, for the times of 30 seconds and 60 seconds. Table 7 also shows the percentage of the total amount of ISF collected in 60 seconds that was collected in the first 30 seconds. This percentage indicates how quickly the rate of collection increases to its maximum and is pertinent because it is desirable for the instrument to collect the fluid in a short amount of time. This example shows that varying the diameter of the aperture at the center of the head can result in significant changes in the volume of fluid collected and flux rates. The smaller the aperture, the faster the ISF is collected, but a lower total volume is collected. At the largest aperture tested (4 mm), the fluid flux rate had significantly decreased, and total volume of ISF collected differed significantly from that when optimum size was used. The optimum size was found to be 2.5 mm to 3.0 mm with these head configurations.

The conditions for forming the micropores in the skin and applying the force to the skin were as follows:

1. Dye #5, ICI 2 mil w/carbon, removed after poration
2. Umbilical porator, 30 pulses, 250 mw
3. 30 ms pulse, 60 ms delay
4. "direct" RAM with 4 lbs. of weight

TABLE 7

| Head | Inside diameter of aperture | Average volume collected, 0–30 sec (µl) | RSD* (%) | Average volume collected, 0–60 sec (µl) | RSD* (%) | Percent of fluid collected in first 30 seconds | Percent of collections >1 µl | Percent of collections >0.5 µl |
|---|---|---|---|---|---|---|---|---|
| C | 1.5 | 0.1033 | 74 | 0.2809 | 49 | 37 | 0 | 0 |
| C | 2.5 | 0.1828 | 70 | 0.5363 | 62 | 33 | 10 | 30 |

TABLE 7-continued

| Head | Inside diameter of aperture | Average volume collected, 0–30 sec (μl) | RSD* (%) | Average volume collected, 0–60 sec (μl) | RSD* (%) | Percent of fluid collected in first 30 seconds | Percent of collections >1 μl | Percent of collections >0.5 μl |
|---|---|---|---|---|---|---|---|---|
| C | 3.0 | 0.1606 | 70 | 0.5106 | 48 | 30 | 10 | 40 |
| C | 4.0 | 0.1225 | 50 | 0.4416 | 32 | 27 | 0 | 30 |
| E | 1.5 | 0.2729 | 54 | 0.6906 | 37 | 37 | 10 | 80 |
| E | 2.5 | 0.4131 | 54 | 1.0747 | 43 | 35 | 70 | 80 |
| E | 3.0 | 0.4369 | 41 | 1.2369 | 33 | 34 | 70 | 100 |
| E | 4.0 | 0.3803 | 47 | 1.2038 | 31 | 31 | 70 | 100 |
| G | 1.5 | 1.2344 | 30 | 1.9556 | 18 | 63 | 100 | 100 |
| G | 2.5 | 1.6919 | 14 | 2.5638 | 11 | 66 | 100 | 100 |
| G | 3.0 | 1.7703 | 20 | 2.6272 | 17 | 67 | 100 | 100 |

*RSD means standard deviation (Std. Dev.) divided by average volume collected times 100%.

Total amount of fluid collected (μl):
Subject 1: 21
Subject 4: 25
Subject 6: 26
Subject 8: 28
Subject 11: 31

Figure 10B:
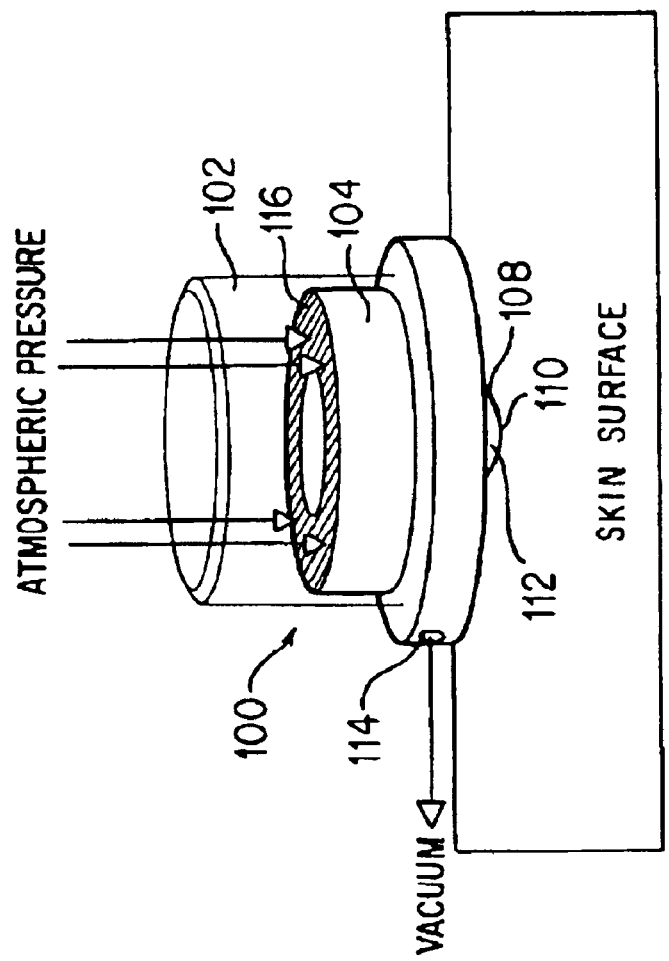
FIGS. 10A and 10B are schematic views of an apparatus that can be used to apply a force to the skin to aid in the collection of interstitial fluids therefrom.
Figure 10A:
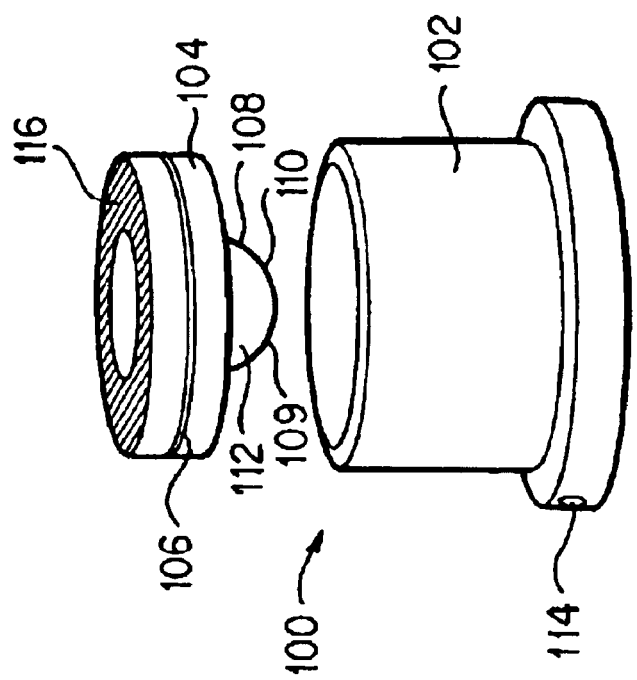

Pressure can be applied to the skin by means of apparatus other than the pressure head and ram previously described. FIGS. 10A and 10B show an apparatus that employs a vacuum to cause atmospheric pressure to act upon a piston in a cylinder and cause it to apply a force to the skin. The apparatus allows the user, i. e., the patient, to apply force to a body part, such as a forearm, without the need for providing an opposing force to inhibit motion.

Typically, when pressure is employed to force interstitial fluids to exude from the skin, a stopping mechanism is required to oppose the applied force and keep the body part stationary. An apparatus that exerts a force on the skin of the forearm normally requires a means for supporting the backside of the arm, typically through the use of a mechanical clamp or an immovable object, such as a table. These means are large and uncomfortable for the user, or they require proper technique to provide consistent results. The apparatus shown in FIGS. 10A and 11B can be made in small sizes. It is less constraining than a clamp or a strap or a band because it does not need to surround the site of interest on the body part. This apparatus is more comfortable than other apparatus currently used to apply force to the skin. Unlike a clamp or a strap or a band, this apparatus will not cause blood vessels to collapse. Because the apparatus requires access to only one surface of a body part of a subject, it can be applied to virtually any site for obtaining samples of interstitial fluids, such as the arm, thigh, or waist, without any modifications.

Figure 11A:
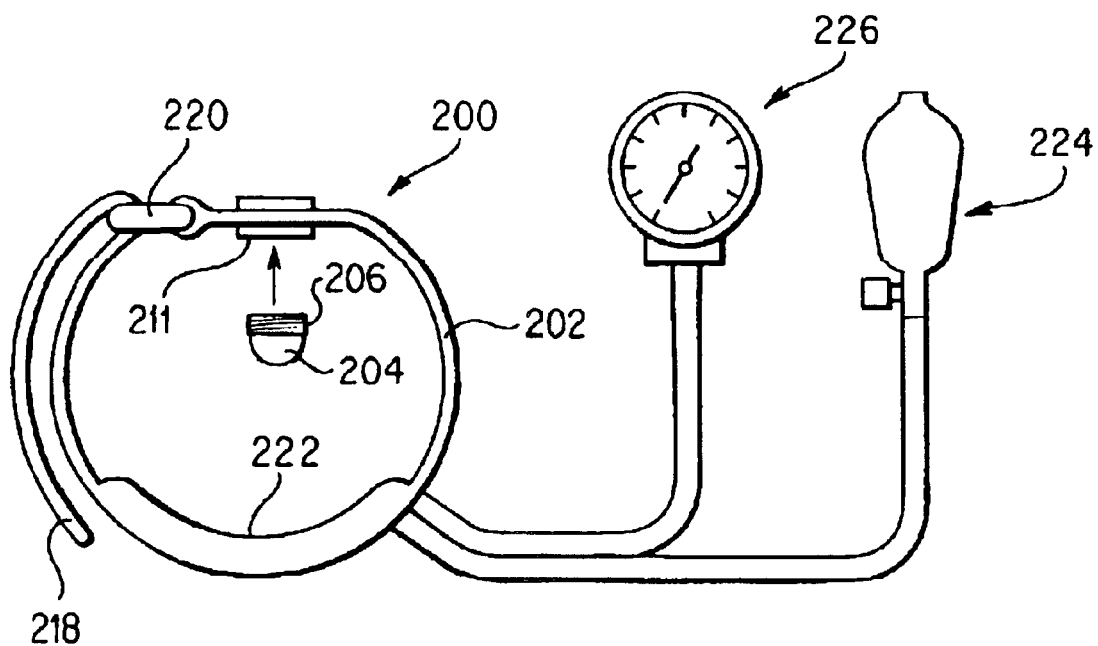
FIGS. 11A and 11B are schematic views of an apparatus that can be used to apply a force to the skin to aid in the collection of interstitial fluids therefrom.
Figure 11B:
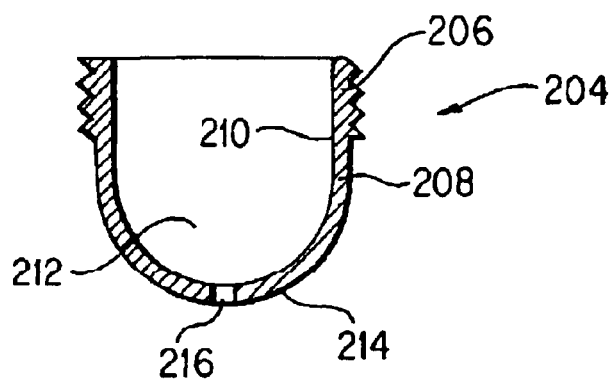

Turning now to FIGS. 10A and 11B, the apparatus 100 comprises a cylinder 102 and a piston 104. The piston 104 comprises a seal 106 and a pressure head 108. The pressure head 108 has a bottom portion 109, which has a small aperture 110 at the lowermost point thereof. The pressure head 108 also contains a reservoir 112. The cylinder 102 has a vacuum port 114. The purpose of the cylinder 102 is to position the apparatus over the site from which interstitial fluids are to be collected. The purpose of the piston 104 is to apply sufficient force to the skin to cause interstitial fluids to emerge therefrom. The purpose of the seal 106 is to maintain the vacuum at a level sufficient for causing the piston 104 to apply sufficient pressure to the skin. The purpose of the pressure head 108 is to provide contact with the skin at the point of application of force. In addition, the pressure head 108 has a small aperture 110, through which the interstitial fluid can flow for collection in the reservoir 112.

In operation, a breach is formed in the stratum corneum by one of the techniques described previously. The apparatus 100 is placed over the breach, with the cylinder 102 being in contact with the skin so that the aperture 110 is in register with the breach in the stratum corneum. The vacuum is applied via a pump or the like (not shown) through the vacuum port 114. Under the influence of vacuum, the piston 104 is caused to travel downwards against the skin because of atmospheric pressure acting on the upper surface 116 of the piston 104. See FIG. 10B. The positive pressure exerted on the skin by the pressure head 108 causes interstitial fluids to flow through the breach in the stratum corneum and through the aperture 110 and collect in the reservoir 112. The fluid can then be analyzed determine the concentration of analyte. Alternatively, the apparatus 100 is placed over the skin, with the cylinder 102 being in contact with the skin. A breach is then formed in the stratum corneum so that the aperture 110 is in register with the breach in the stratum corneum. If desired, pressure can be applied to the skin prior to forming the breach in the stratum corneum. The vacuum is applied via a pump or the like (not shown) through the vacuum port 114. Under the influence of vacuum, the piston 104 is caused to travel downwards against the skin because of atmospheric pressure acting on the upper surface 116 of the piston 104. See FIG. 10B. The positive pressure exerted on the skin by the pressure head 108 causes interstitial fluids to flow through the breach in the stratum corneum and through the aperture 110 and collect in the reservoir 112. The fluid can then be analyzed determine the concentration of analyte. Variations of these specific procedures can also be used.

A pressure cuff can be used to apply force and pressure to a body part in which a breach of the stratum corneum has been formed so that interstitial fluids can be collected from the breach. In appearance, the pressure cuff is substantially similar to the pressure cuffs used to measure a person's blood pressure. In other words, the pressure cuff comprises a strap or band that is designed to surround the site of interest on the body part. Referring now to FIGS. 11A and 11B, a pressure cuff 200 comprises a band 202 to which is attached a pressure head 204. The purpose of the pressure head 204 is to provide contact with the skin at the point of application of force. At one end of the pressure head 204 are means 206 for attaching the pressure head 204 to the band 202. Such means 206 may include threads; preferably the threads are on the exterior wall 208 of the pressure head 204, although the threads may also be along the interior wall 210 of the pressure head 204. The band 202 comprises a means 211 for securing the pressure head 204. If the pressure head 204 utilizes threads, the securing means 211 preferably also uses threads. The interior of the pressure head 204 forms a reservoir 212. At the end opposite the means 206 for attaching the head 204 to the band 202 is a bottom portion 214 which may be circular, elliptical, square, rectangular or other shape. An aperture 216 is formed through the bottom portion 214 to form a communication channel to the reservoir 212.

In operation, a breach is formed in the stratum corneum of the body part, preferably the forearm, by one of the techniques described previously. The band 202 is placed around the body part so that the pressure head 204 is directly over the breach, so that the aperture 216 is in register with the breach in the stratum corneum. The band 202 has an end 218, which is inserted through a buckle 220. The end 218 of the band 202 can be pulled to tighten the band 202 around the site of interest on the body part. The band 202 can be tightened further by increasing the pressure within a bladder 222, located on the band 202. The pressure can be increased in the bladder 222 by supplying air from a pump 224. The increase in pressure can be monitored by a pressure gauge 226. The band 202 should be tightened sufficiently so that the pressure head 204 applies a force to the skin sufficient to cause interstitial fluids to flow through the breach in the stratum corneum and through the aperture 216 and collect in the reservoir 212. The fluid can then be analyzed determine the concentration of an analyte.

Alternatively, the band 202 is placed around the body part. A breach is formed in the stratum corneum of the body part, preferably the forearm, so that the aperture 216 is in register with the breach in the stratum corneum. If desired, pressure can be applied to the skin prior to forming the breach in the stratum corneum. The end 218 of the band 202 can be pulled to tighten the band 202 around the site of interest on the body part. The band 202 can be tightened further by increasing the pressure within a bladder 222, located on the band 202. The pressure can be increased in the bladder 222 by supplying air from a pump 224. The increase in pressure can be monitored by a pressure gauge 226. The band 202 should be tightened sufficiently so that the pressure head 204 applies a force to the skin sufficient to cause interstitial fluids to flow through the breach in the stratum corneum and through the aperture 216 and collect in the reservoir 212. The fluid can then be analyzed determine the concentration of analyte. Variations of these specific procedures can also be used.

Upon reading and understanding the invention disclosed herein, it should be apparent to those of skill in the art that modifications and changes to the apparatus and methods disclosed herein can be made while still falling within the scope and spirit of the present invention. All such modifications and changes are included herein and the invention should be considered limited only by the claims which follow hereafter.

What is claimed is:

1. An apparatus for the collection of interstitial fluids from the body of an animal, comprising:

a pressure head having a top portion and a bottom portion, with an exterior wall and an interior wall extending therebetween, said top portion having the major dimension thereof at least as great as the major dimension of said bottom portion;

an aperture extending through said bottom portion and in fluid communication with a reservoir;

said aperture having an area less than the area of said bottom portion, said aperture having a major dimension of from about 2.5 mm to about 3.0 mm.

2. The apparatus of claim 1, further including a holder for mating engagement with said pressure head, said holder including a drive connectable with said pressure head, said drive adapted to supply a force to said pressure head in a direction from said top portion toward said bottom portion.

3. The apparatus of claim 1, wherein the top portion of said pressure head comprises a threaded end.

4. A method for the collection of interstitial fluids from the body of an animal, comprising the steps of:

forming a breach through the stratum corneum of the animal, said breach extending at least into the epidermal layer of the skin of the animal;

placing the pressure head of claim 1 adjacent to said breach;

exerting a positive pressure on said head in a direction generally toward the skin of the animal; and collecting fluids from said breach.

5. The method of claim 4, wherein the step of forming a breach comprises forming at least one micropore through said stratum corneum.

6. The method of claim 4, wherein the pressure head applies a force ranging from about 1 to about 11 pounds.

7. A method for the collection of interstitial fluids from the body of an animal, comprising the steps of:

placing the pressure head of claim 1 against the skin of the animal;

forming a breach through the stratum corneum of the animal, said breach extending at least into the epidermal layer of the skin of the animal, said breach adjacent to said pressure head;

exerting a positive pressure on said head in a direction generally toward the skin of the animal; and collecting fluids from said breach.

8. The method of claim 7, wherein the step of forming a breach comprises forming at least one micropore through said stratum corneum.

9. The method of claim 7, wherein the pressure head applies a force ranging from about 1 to about 11 pounds.

10. The method of claim 7, wherein said pressure head applies a force prior to the formation of said breach.

11. A method for the collection of interstitial fluids from the body of an animal, comprising the steps of:

forming a breach through the stratum corneum of the animal, said breach extending at least into the epidermal layer of the skin of the animal;

exerting a positive pressure adjacent to said breach in a direction generally toward the skin of the animal, said positive pressure being exerted by means of the pressure head of claim 1; and collecting fluids from said breach.

12. The method of claim 11, wherein the step of forming a breach comprises forming at least one micropore through said stratum corneum.

13. The method of claim 12, wherein the positive pressure exerted involves a force ranging from about 1 to about 11 pounds.

* * * * *